United States Patent
Ham et al.

(10) Patent No.: US 9,650,355 B2
(45) Date of Patent: May 16, 2017

(54) METHOD FOR PREPARATION OF JUSTICIDIN A DERIVATIVES OF ARYLNAPHTHALENE LIGNAN STRUCTURE

(71) Applicant: Korea Institute of Science and Technology, Seoul (KR)

(72) Inventors: Jungyeob Ham, Gangneung-si (KR); Tae Jung Kim, Seoul (KR); Hak Cheol Kwon, Seoul (KR); Kyu Hyuk Jeong, Donghae-si (KR); Jungho Song, Gangneung-si (KR); Bong Chul Chung, Namyangju-si (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 14/760,400

(22) PCT Filed: Jan. 28, 2014

(86) PCT No.: PCT/KR2014/000767
§ 371 (c)(1),
(2) Date: Jul. 10, 2015

(87) PCT Pub. No.: WO2014/119892
PCT Pub. Date: Aug. 7, 2014

(65) Prior Publication Data
US 2015/0336938 A1    Nov. 26, 2015

(30) Foreign Application Priority Data
Jan. 31, 2013 (KR) .................. 10-2013-0011137

(51) Int. Cl.
*C07D 407/04* (2006.01)
*C07D 409/04* (2006.01)
*C07D 307/88* (2006.01)
*C07D 405/04* (2006.01)
*C07D 493/04* (2006.01)

(52) U.S. Cl.
CPC ......... *C07D 307/88* (2013.01); *C07D 405/04* (2013.01); *C07D 407/04* (2013.01); *C07D 409/04* (2013.01); *C07D 493/04* (2013.01)

(58) Field of Classification Search
CPC ........................... C07D 407/04; C07D 409/04
See application file for complete search history.

(56) References Cited

U.S. PATENT DOCUMENTS

| 4,486,445 A | 12/1984 | Patel et al. |
| 2013/0012727 A1 | 1/2013 | Mulik et al. |

FOREIGN PATENT DOCUMENTS

| JP | 2012-516886 A | 7/2012 |
| WO | WO 94/05658 A1 | 3/1994 |
| WO | WO 2010-089778 A2 | 8/2010 |

OTHER PUBLICATIONS

International Search Report issued on May 20, 2014 in counterpart International Application No. PCT/KR2014/000767 (3 pages, in English).
Padwa, Albert, John E. Cochran, and C. Oliver Kappe. "Tandem Pummerer-Diels-Alder Reaction Sequence. A Novel Cascade Process for the Preparation of 1-Arylnaphthalene Lignans." *The Journal of organic chemistry* 61.11 (1996): 3706-3714. (9 pages, in English).
Pan, Jian-Yu, et al., "An update on lignans: natural products and synthesis." *Natural product reports* 26.10 (2009): 1251-1292. (42 pages, in English).
Sato, Yoshihiro, Takayuki Tamura, and Miwako Mori. "Arylnaphthalene Lignans through Pd-Catalyzed [2+2+2] Cocyclization of Arynes and Diynes: Total Synthesis of Taiwanins C and E." *Angewandte Chemie International Edition* 43.18 (2004): 2436-2440. (5 pages, in English).
Ward, R. S. "The synthesis of lignans and neolignans." *Chemical Society Reviews* 11.2 (1982): 75-125. (51 pages, in English).
Yu, Zhao, et al. "Synthesis and bioevaluation of novel analogues of justicidin A." *Medicinal chemistry research* 19.1 (2010): 71-76. (6 pages, in English).

*Primary Examiner* — Shawquia Jackson
(74) *Attorney, Agent, or Firm* — NSIP Law

(57) ABSTRACT

The present disclosure relates to a novel method for preparing an arylnaphthalene lignan compound. In synthesis of arylnaphthalene lignan compounds and derivatives according to the present disclosure, a naphthalene backbone may be constructed first and an aryl group may be introduced at the final stage. Through this, various kinds of derivatives that could not be prepared from the existing methods can be synthesized effectively. Further, the synthesis method according to the present disclosure is appropriate for large-scale production.

14 Claims, No Drawings

METHOD FOR PREPARATION OF JUSTICIDIN A DERIVATIVES OF ARYLNAPHTHALENE LIGNAN STRUCTURE

CROSS-REFERENCE TO RELATED APPLICATIONS

This application claims the benefit under 35 USC 371 of International Application No. PCT/KR2014/000767 filed on Jan. 28, 2014, which claims the benefit of Korean Application No. 10-2013-0011137 filed on Jan. 31, 2013 in the Korean Intellectual Property Office, the entire disclosures of which are incorporated herein by reference for all purposes.

TECHNICAL FIELD

The present disclosure relates to a novel method for preparing an arylnaphthalene lignan compound.

BACKGROUND ART

Until now, researches about synthesis of the multi-substituted naphthalene lactone backbone of arylnaphthalene lignan-based natural products have been carried out in 4 ways as described below.

1. Tandem Horner-Emmons-Claisen condensation

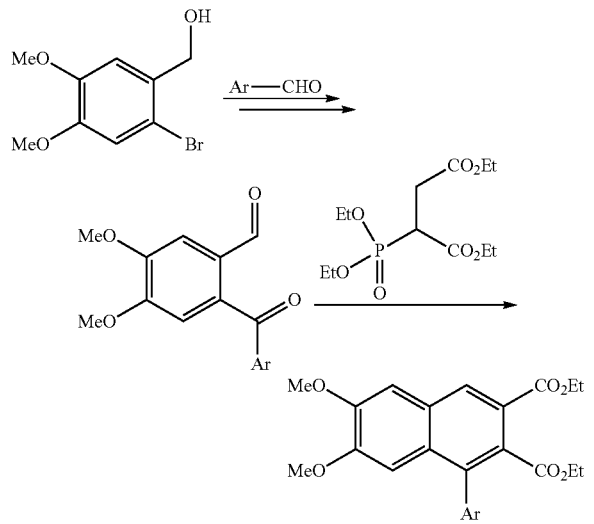

2. Diels-Alder addition

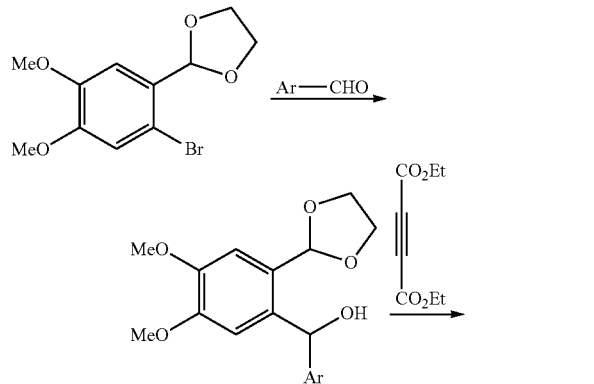

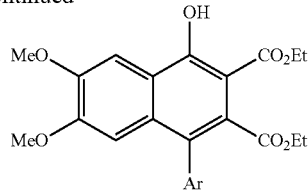

3. Palladium-catalyzed [2 + 2 + 2] cycloaddition

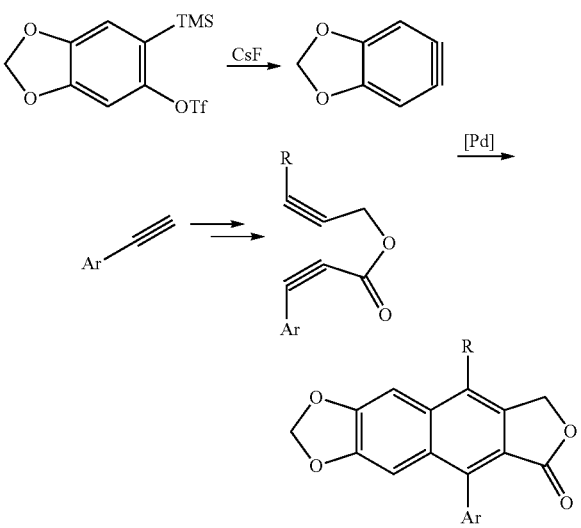

4. Gold-catalyzed intramolecular sequential electrophilic addition and benzannulation

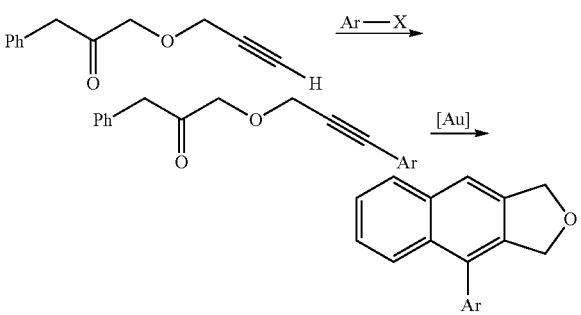

In the synthesis methods based on tandem Horner-Emmons-Claisen condensation and Diels-Alder addition, an Ar group is introduced in the initial stage of synthesis and, after a naphthalene backbone is formed under strongly basic or acidic conditions, a lactone structure is formed in the final stage using a reducing agent. Accordingly, use of Ar groups that are reactive under strongly basic or acidic conditions and in the presence of a reducing agent is limited. Also, in the synthesis methods based on palladium-catalyzed [2+2+2] cycloaddition and gold-catalyzed intramolecular sequential electrophilic addition and benzannulation, since an Ar group is introduced in the initial stage of synthesis, the methods are limited to Ar groups which are not reactive in the presence of the palladium or gold catalyst. Besides, it is impossible to selectively obtain the desired products since the position of the carbonyl group of lactone cannot be controlled.

That is to say, all the methods known thus far, including the above representative synthesis methods, involve addition of Ar groups having aldehyde, alkyne or aryl halide groups in the early stage of synthesis. Accordingly, these methods are not effective for synthesis of arylnaphthalene lignan derivatives and are applicable only to limited types of arylnaphthalene lignan compounds that can endure the reaction conditions of several steps until the final compounds are obtained.

The inventors of the present disclosure have invented a method allowing preparation of various kinds of arylnaphthalene lignan compounds without such limitations.

DISCLOSURE

Technical Problem

The present disclosure is directed to providing a method allowing effective preparation of various kinds of arylnaphthalene lignan compounds and derivatives with high yield.

Technical Solution

In a general aspect, there is provided a method for preparing an arylnaphthalene lignan compound, including Scheme A:

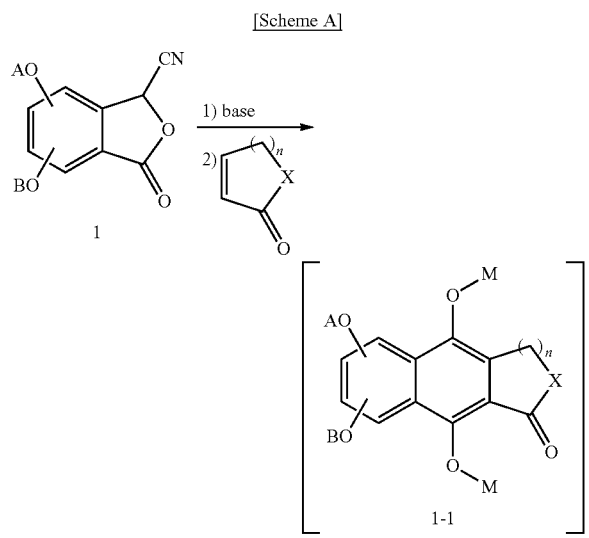

wherein
each of A and B is independently $C_1$-$C_8$ alkyl or $C_2$-$C_9$ alkylether or A and B are linked via methylene to form a heterocycle;
X is —O, —$NR^1$ or —$CH_2$—;
n is 1 or 2;
$R^1$ is $C_1$-$C_8$ alkyl or $C_7$-$C_{14}$ arylalkyl; and
M is lithium, potassium or sodium.

Advantageous Effects

In synthesis of arylnaphthalene lignan compounds and derivatives according to the present disclosure, a naphthalene backbone may be constructed first and an aryl group may be introduced at the final stage. Through this, various kinds of derivatives that could not be prepared from the existing methods can be synthesized effectively. Further, the synthesis method according to the present disclosure is appropriate for large-scale production.

Best Mode

The present disclosure provides a method for preparing an arylnaphthalene lignan compound, including Scheme A:

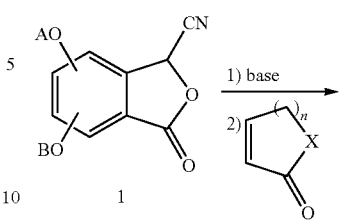

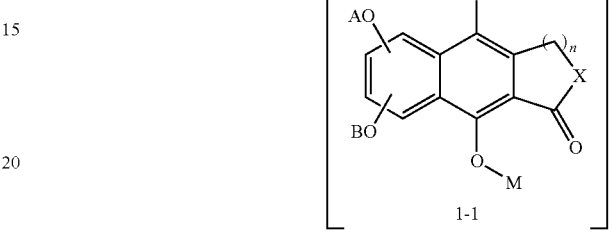

wherein
each of A and B is independently C1-C8 alkyl or C2-C9 alkylether or A and B are linked via methylene to form a heterocycle;
X is —O, —NR1 or —CH2—;
n is 1 or 2;
R1 is C1-C8 alkyl or C7-C14 arylalkyl; and
M is lithium, potassium or sodium.

Scheme A may sequentially include (i) Michael reaction, (ii) aldol reaction and (iii) benzannulation. In the present disclosure, the Michael reaction refers to a reaction whereby a nucleophile is added to an α,β-unsaturated carbonyl compound in the presence of a base. In the present disclosure, the aldol reaction refers, for example, a reaction whereby two acetaldehyde molecules react with each other in the presence of a base form an aldol. In the present disclosure, the benzannulation refers to a reaction whereby a benzene ring is formed.

In Scheme A, the compound of Chemical Formula 1 may be reacted with an α, β-unsaturated carbonyl compound [see step 2) in Scheme A] via Michael reaction and then aldol reaction may be carried out.

Scheme A may be carried out using a solvent such as diethyl ether, tetrahydrofuran, etc. The base used in Scheme A may be selected appropriately according to the reaction solvent. Specifically, lithium bis(trimethylsilyl)amide, potassium bis(trimethylsilyl)amide, sodium bis(trimethylsilyl)amide, lithium t-butoxide, potassium t-butoxide, sodium t-butoxide, lithium diisopropylamide, s-butyllithium, t-butyllithium, etc. may be used. And, in Scheme A, the α,β-unsaturated carbonyl compound may be used in an amount of specifically 1.0-3.0 equivalents, more specifically 1.5-2.0 equivalents. The compound of Chemical Formula 1-1 may be obtained with high yield when the α,β-unsaturated carbonyl compound is used in the above-described amount. The steps 1) and 2) of Scheme A may be carried out at −50 to −80° C. for 1-10 hours, specifically at −78° C. for 6 hours, but is not limited thereto. The reaction temperature and reaction time of Scheme A may vary depending on reactants.

An example of Scheme A is as follows.

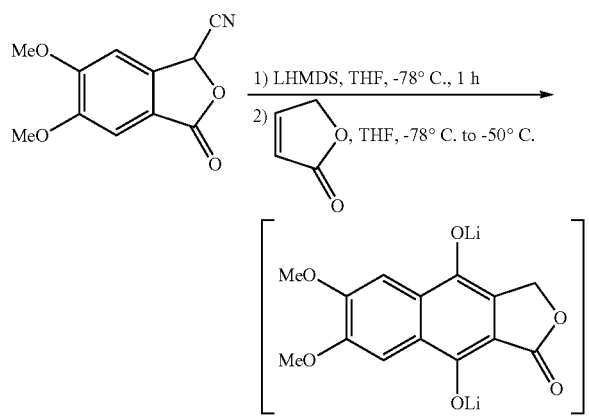

In the present disclosure, the compound of Chemical Formula 1 which is a reactant in Scheme A may be prepared as follows. However, any method obvious to those skilled in the art may be used without being limited thereto and the compound may also be purchased commercially. For example, the compound of Chemical Formula 1 may be prepared as follows, but is not limited thereto.

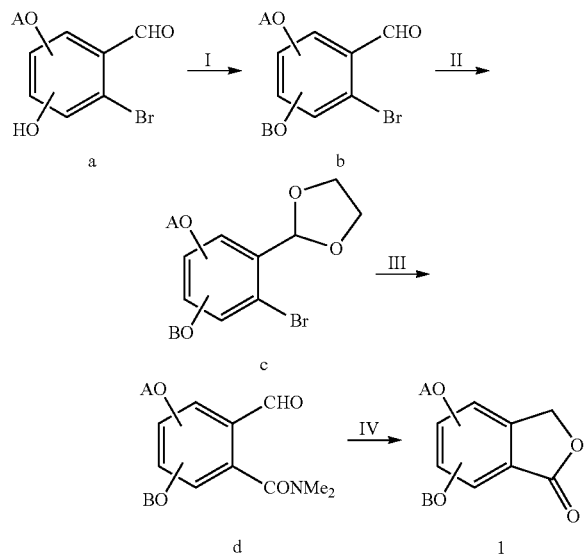

The compound of Chemical Formula 1 may be obtained from the compound d via Scheme IV or from the compound c via Schemes III and IV. Alternatively, the compound of Chemical Formula 1 may be obtained from the compound b via Schemes II, III and IV or from the compound a via Schemes I, II, III and IV. The compounds a-d may be purchased commercially or prepared according to a method known in the art.

Specifically, the compound of Chemical Formula 1 may be obtained from the compound d via Scheme IV. The compound of Chemical Formula 1 may be prepared by reacting the compound d with cyanohydrin and then adding an acid.

In Scheme IV, for example, chloroform, dichloromethane or carbon tetrachloride may be used as a solvent. The cyanohydrin reagent may include potassium cyanide (KCN) or trimethylsilyl cyanide (TMSCN) and 18-crown-6 may be added to dissolve the KCN.

The reaction temperature of Scheme IV may vary depending on the solutes used but may be specifically 25-40° C. in general. Also, the reaction temperature may vary depending on the solutes used but may be specifically 2-12 hours.

The reaction of Scheme IV is a one-pot reaction. The acid used in the reaction may be selected adequately depending on the solutes used. Specifically, a carboxylic acid such as acetic acid, formic acid, etc., a sulfonic acid such as camphorsulfonic acid (CSA), p-toluenesulfonic acid, trifluoromethanesulfonic acid, pyridinium p-toluenesulfonate, etc., hydrochloric acid, sulfuric acid or nitric acid may be used. The reaction temperature when the acid is added may vary may vary depending on the solutes used but may be specifically 25-40° C. The reaction time may also vary depending on the reaction temperature and the solvent used but may be specifically 1-24 hours.

An example of Scheme IV is as follows.

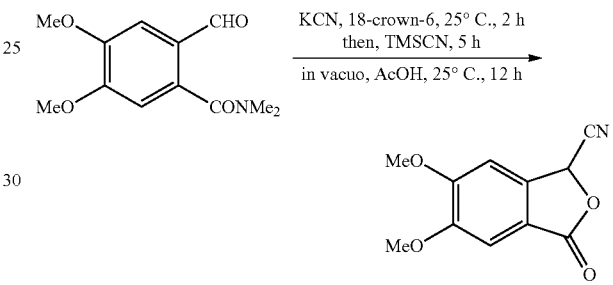

Specifically, the compound d may be obtained from the compound c via Scheme III. In Scheme III, the compound c may be treated with an alkyllithium reagent and N,N-dialkylcarbamoyl chloride and then an aqueous acid solution may be added.

When treating with the alkyllithium reagent, diethyl ether, tetrahydrofuran, etc. may be used as a solvent. The alkyllithium reagent may be selected adequately depending on the solutes. Specifically, n-butyllithium, s-butyllithium, t-butyllithium or phenyllithium may be used. And, the N,N-dialkylcarbamoyl chloride may include N,N-dimethylcarbamoyl chloride, N,N-diethylcarbamoyl chloride and N,N-diisopropylcarbamoyl chloride. The reaction temperature when treating with the alkyllithium reagent may be determined depending on the solutes used. Specifically, the reaction may be carried out by starting at −80 to 25° C. and increasing temperature to 80° C. More specifically, the reaction may be carried out between −78° C. and 25° C. The reaction may be carried out specifically for 1-24 hours, more specifically for 5 hours.

The acid used in Scheme III is not particularly limited as long as it can be used for acetal deprotection of oxolane via a one-pot reaction. Specifically, an aqueous solution of a sulfonic acid such as camphorsulfonic acid (CSA), p-toluenesulfonic acid (p-TsOH), trifluoromethanesulfonic acid (TfOH), pyridinium p-toluenesulfonate, etc., hydrochloric acid, sulfuric acid or nitric acid may be used. The reaction temperature may vary depending on the solutes used but may be specifically −20 to 40° C. The reaction time may also vary depending on the reaction temperature and the solvent used but may be specifically, 10 minutes to 2 hours.

An example of Scheme III is as follows.

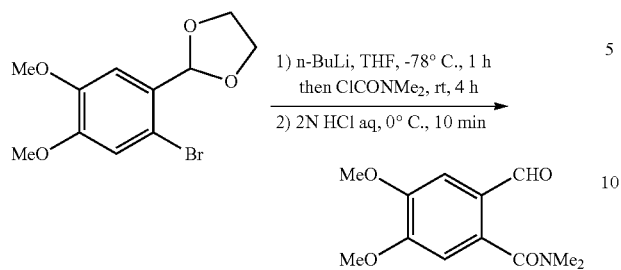

Specifically, the compound c may be obtained from the compound b via Scheme II. The reaction of Scheme II is not particularly limited as long as the aldehyde group of the compound b can be protected thereby. As a typical example of a reaction for protecting the aldehyde group, the compound b may be reacted with ethylene glycol under acidic condition.

In Scheme II, an anhydrous aromatic hydrocarbon such as benzene, toluene, xylene, etc. may be used as a solvent. And, the acid used in Scheme II may be selected appropriately depending on the solutes. Specifically, camphorsulfonic acid (CSA), p-toluenesulfonic acid, trifluoromethanesulfonic acid or pyridinium p-toluenesulfonate may be used. Scheme II may be carried out at 25-120° C. for 1-24 hours, more specifically at 80° C. for 3 hours.

An example of Scheme II is as follows.

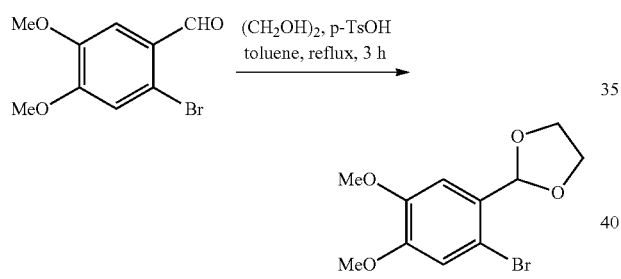

Specifically, the compound b may be obtained from the compound a via Scheme I. The reaction of Scheme I is not particularly limited as long as the phenolic hydroxyl group of the compound a can be protected thereby.

Specifically, an alkylether protecting group such as methyl, ethyl, t-butyl, benzyl, methoxymethyl, etc., or a silyl protecting group such as trimethylsilyl, t-butyldiphenylsilyl, t-butyldimethylsilyl, triisopropylsilyl, etc. may be used as a protecting group of the phenolic hydroxyl group. In Scheme I, an aprotic anhydrous polar solvent such as N,N-dimethylformamide, N,N-dimethylacetamide, dimethyl sulfoxide, acetonitrile, acetone, etc., an anhydrous ether solvent such as dioxane, dimethoxyethane, etc. or an anhydrous aromatic hydrocarbon solvent such as benzene, toluene, xylene, etc. may be used. In Scheme I, an alkali metal hydride such as sodium hydride, lithium hydride, etc., an alkaline earth metal hydride such as calcium hydride, an alkali metal hydroxide such as sodium hydroxide, potassium hydroxide, etc. or an alkali metal carbonate such as lithium carbonate, potassium carbonate, potassium bicarbonate, etc. may be used as a base. The reaction temperature of Scheme I may vary depending on the protecting group or the solvent used. Specifically, the reaction may be carried out at 25-40° C. for 30 minutes to 24 hours.

In the preparation method according to the present disclosure, the base may be one or more selected from a group consisting of lithium bis(trimethylsilyl)amide, potassium bis(trimethylsilyl)amide, sodium bis(trimethylsilyl)amide, lithium t-butoxide, potassium t-butoxide, sodium t-butoxide, lithium diisopropylamide, s-butyllithium and t-butyllithium.

In the preparation method according to the present disclosure, the arylnaphthalene lignan compound may have a structure of Chemical Formula 6 or 9:

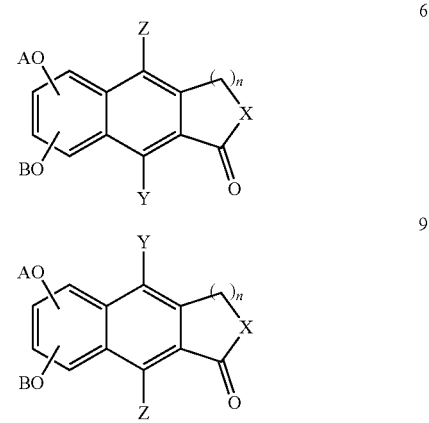

wherein
Y is hydroxyl, sulfonate,

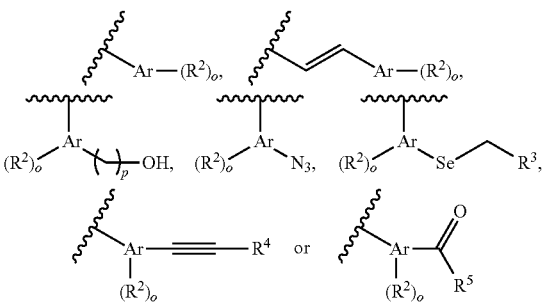

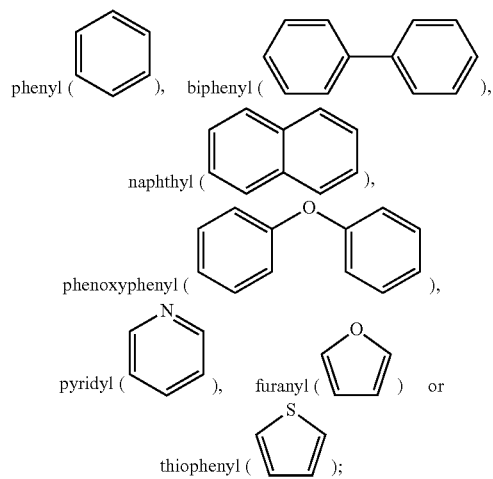

wherein
Ar is

R² is hydrogen, C₁-C₈ alkyl, C₁-C₄ alkyloxy, C₁-C₄ alkylether, C₁-C₄ alkylthiooxy, vinyl, C₃-C₈ alkylvinyl, hydroxyl, nitro (—NO₂), fluoro, chloro, cyano, formyl (—CHO), C₂-C₁₂ acyl, C₁-C₅ alkylester or C₇-C₁₀ arylester;

R³ is C₁-C₁₀ alkyl, C₆-C₁₂ aryl, C₇-C₁₀ alkylaryl, C₂-C₁₀ arylalkyl, C₁-C₄ alkylether, C₁-C₅ alkylester or C₂-C₁₂ acyl;

R⁴ is hydrogen, C₁-C₆ alkyl, C₇-C₁₂ cyclohexylalkyl, C₇-C₁₂ arylalkyl, C₂-C₆ alkylether, C₂-C₆ alkylthioether, C₂-C₆ alkylcyano, C₁-C₄ alkylalcohol or

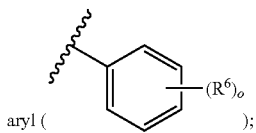

aryl ( (R⁶)ₒ );

R⁵ is independently hydrogen, C₁-C₆ alkyl, C₇-C₁₂ cyclohexylalkyl, C₇-C₁₂ arylalkyl, C₂-C₆ alkylether, C₂-C₆ alkylthioether, C₂-C₆ alkylcyano, C₁-C₄ alkylalcohol or

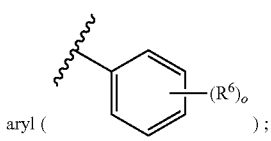

aryl ( (R⁶)ₒ );

R⁶ is hydrogen, C₁-C₆ alkyl, C₇-C₁₀ alkylaryl, C₁-C₄ alkylether, C₁-C₄ alkylthioether, fluoro or chloro;
o is an integer from 1 to 5; and
p is an integer from 0 to 2, and
Z is O—R⁷,

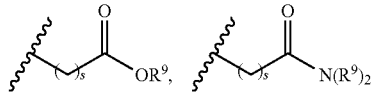

or glycosyl
wherein
R⁷ is hydrogen, C₁-C₈ alkyl, C₂-C₉ alkylether, C₁-C₅ alkylester, C₇-C₁₀ arylester or

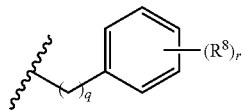

R⁸ is C₁-C₄ alkyl, C₁-C₄ alkyloxy, nitro (—NO₂), cyano (—CN), fluoro, chloro, bromo, iodo or hydrogen;
q is an integer from 0 to 5;
r is an integer from 1 to 4;
R⁹ is C₁-C₈ alkyl or hydrogen;
s is an integer from 1 to 5; and
the glycosyl group is 4-O-β-D-galactopyranosyl, 4-O-α-L-arabinosyl, 4-O-β-D-glucopyranosyl, 4-O-β-D-xylosyl, 6·-O-methyl-4-O-β-D-glucopyranosyl, 6·-O-methyl-4-O-β-D-galactopyranosyl, 4-O-β-D-fucopyranosyl, 6·-O-benzyl-4-O-β-D-glucopyranosyl or 6·-O-benzyl-4-O-β-D-galactopyranosyl.

In the preparation method according to the present disclosure, the arylnaphthalene lignan compound may be 9-(benzo[d][1,3]dioxol-5-yl)-4,6,7-trimethoxynaphtho[2,3-c]furan-1(3H)-one (justicidin A), t-butyl 9-hydroxy-6,7-dimethoxy-1-oxo-1,3-dihydronaphtho[2,3-c]furan-4-yl carbonate, 9-(t-butoxycarbonyloxy)-6,7-dimethoxy-3-oxo- 1,3-dihydronaphtho[2,3-c]furan-4-yl trifluoromethanesulfonate, 9-(benzo[d][1,3]dioxol-5-yl)-6,7-dimethoxy-1-oxo-1,3-dihydronaphtho[2,3-c]furan-4-yl t-butylcarbonate, 9-(benzo[d][1,3]dioxol-5-yl)-4-hydroxy-6,7-dimethoxynaphtho[2,3-c]furan-1(3H)-one (diphyllin), 9-(3,4-dimethoxyphenyl)-4,6,7-trimethoxynaphtho[2,3-c]furan-1 (3H)-one (cilinaphthalide B), t-butyl 9-(3,4-dimethoxyphenyl)-6,7-dimethoxy-1-oxo-1,3-dihydronaphtho[2,3-c]furan-4-yl carbonate, 9-(3,4-dimethoxyphenyl)-4-hydroxy-6,7-dimethoxynaphtho[2,3-c]furan-1 (3H)-one, 9-(3,5-dimethoxyphenyl)-4,6,7-trimethoxynaphtho[2,3-c]furan-1 (3H)-one, t-butyl 9-(3,5-dimethoxyphenyl)-6,7-dimethoxy-1-oxo-1,3-dihydronaphtho[2,3-c]furan-4-yl carbonate, 9-(3, 5-dimethoxyphenyl)-4-hydroxy-6,7-dimethoxynaphtho[2,3-c]furan-1 (3H)-one, 4,6,7-thmethoxy-9-(4-methoxyphenyl)naphtho[2,3-c]furan-1 (3H)-one, t-butyl 6,7-dimethoxy-9-(4-methoxyphenyl)-1-oxo-1,3-dihydronaphtho[2,3-c]furan-4-yl carbonate, 4-hydroxy-6,7-dimethoxy-9-(4-methoxyphenyl)naphtho[2,3-c]furan-1 (3H)-one, 4,6,7-trimethoxy-9-phenylnaphtho[2,3-c]furan-1 (3H)-one, t-butyl 6,7-dimethoxy-1-oxo-9-phenyl-1,3-dihydronaphtho[2,3-c]furan-4-yl carbonate, 4-hydroxy-6,7-dimethoxy-9-phenylnaphtho[2,3-c]furan-1 (3H)-one, 4,6,7-dimethoxy-9-(4-vinylphenyl)naphtho[2,3-c]furan-1 (3H)-one, t-butyl 6,7-dimethoxy-1-oxo-9-(4-vinylphenyl)-1,3-dihydronaphtho[2, 3-c]furan-4-yl carbonate, 4-hydroxy-6,7-dimethoxy-9-(4-vinylphenyl)naphtho[2,3-c]furan-1 (3H)-one, 9-(4-fluorophenyl)-4,6,7-trimethoxynaphtho[2,3-c]furan-1 (3H)-one, t-butyl 9-(4-fluorophenyl)-6,7-dimethoxy-1-oxo-1,3-dihydronaphtho[2,3-c]furan-4-yl carbonate, 9-(4-fluorophenyl)-4-hydroxy-6,7-dimethoxynaphtho[2,3-c]furan-1 (3H)-one, 4-(9-hydroxy-6,7-dimethoxy-3-oxo-1,3-dihydronaphtho[2,3-c]furan-4-yl)benzonitrile, t-butyl 9-(4-cyanophenyl)-6,7-dimethoxy-1-oxo-1,3-dihydronaphtho[2, 3-c]furan-4-yl carbonate, 4-(9-hydroxy-6,7-dimethoxy-3-oxo-1,3-dihydronaphtho[2,3-c]furan-4-yl)benzonitrile, 9-(4-acetylphenyl)-4,6,7-trimethoxynaphtho[2,3-c]furan-1 (3H)-one, 9-(4-acetylphenyl)-6,7-dimethoxy-1-oxo-1,3-dihydronaphtho[2,3-c]furan-4-yl t-butylcarbonate, 9-(4-acetylphenyl)-4-hydroxy-6,7-dimethoxynaphtho[2,3-c]furan-1 (3H)-one, 4,6,7-trimethoxy-9-(thiophen-3-yl)naphtho[2,3-c]furan-1 (3H)-one, 4-hydroxy-6,7-dimethoxy-9-(thiophen-3-yl)naphtho[2,3-c]furan-1 (3H)-one, 9-(furan-3-yl)-4,6,7-trimethoxynaphtho[2,3-c]furan-1 (3H)-one, t-butyl 9-(furan-3-yl)-6,7-dimethoxy-1-oxo-1,3-dihydronaphtho[2,3-c]furan-4-yl carbonate, 9-(furan-3-yl)-4-hydroxy-6,7-dimethoxynaphtho[2,3-c]furan-1 (3H)-one, (E)-4,6,7-trimethoxy-9-styrylnaphtho[2,3-c]furan-1 (3H)-one, (E)-4-hydroxy-6,7-dimethoxy-9-styrylnaphtho[2,3-c]furan-1 (3H)-one, 5-(1,3-benzodioxol-5-yl)-9-methoxy-furo [3',4':6,7]naphtho[2,3-d]-1,3-dioxol-6(8H)-one (justicidin F, taiwanin E methyl ether), t-butyl 9-hydroxy-1-oxo-1,3-dihydronaphtho[2,3-d]-1,3-dioxol[2,3-c]furan-4-yl carbonate, 9-(t-butoxycarbonyloxy)-3-oxo-1,3-dihydronaphtho[2,3-d]-1,3-dioxol[2,3-c]furan-4-yl trifluoromethanesulfonate, 9-(benzo[d][1,3]dioxol-5-yl)-1-oxo-1,3-dihydronaphtho[2, 3-d]-1,3-dioxol[2,3-c]furan-4-yl t-butylcarbonate, 5-(1,3-benzodioxol-5-yl)-9-hydro-furo[3',4':6,7]naphtho[2,3-d]-1, 3-dioxol-6(8H)-one (taiwanin E), 4-(benzo[d][1,3]dioxol-5-yl)-6,7,9-trimethoxynaphtho[2,3-c]furan-1 (3H)-one (justicidin C), 9-hydroxy-6,7-dimethoxy-1-oxo-1,3-dihydronaphtho[2,3-c]furan-4-yl methanesulfonate, 6,7,9-trimethoxy-1-oxo-1,3-dihydronaphtho[2,3-c]furan-4-yl methanesulfonate or 9-benzo[1,3]dioxol-5-yl-4,6,7-trimethoxy-2-methyl-2,3-dihydro-benzo[f]isoindol-1-one.

Exemplary structures of the arylnaphthalene lignan compound are as follows.

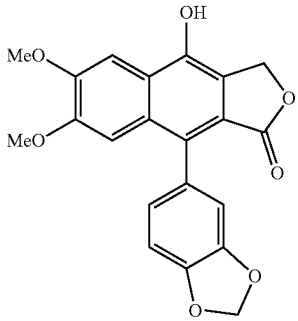

Diphyllin

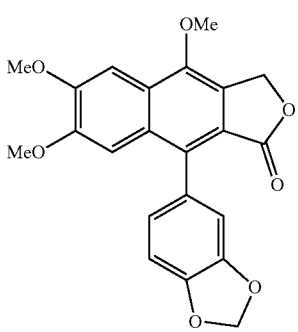

Justicidin A

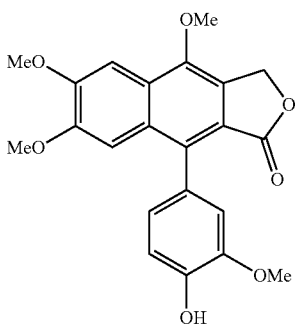

Cilinaphthalide A

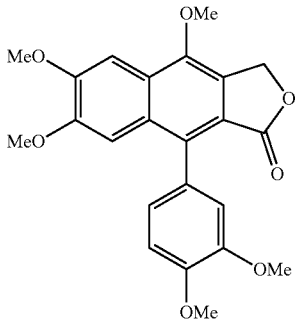

Cilinaphthalide B

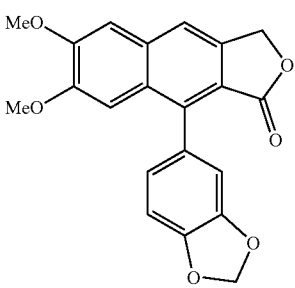

Justicidin B

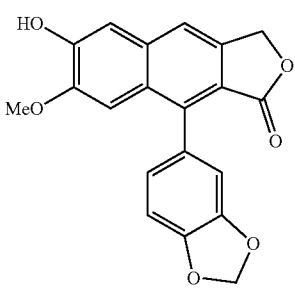

Daurinol

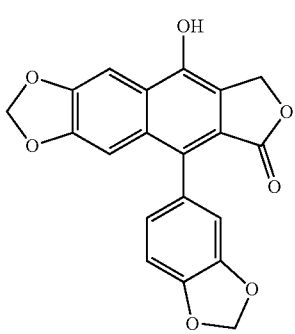

Taiwanin E

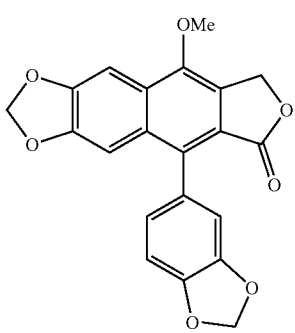

Justicidin F

In the preparation method according to the present disclosure, if X in Scheme A is O, the compound of Chemical Formula 2 may be sequentially subjected to ring opening and lactam formation reactions to prepare a nitrogen-containing lactam ring.

An example of the reaction is as follows.

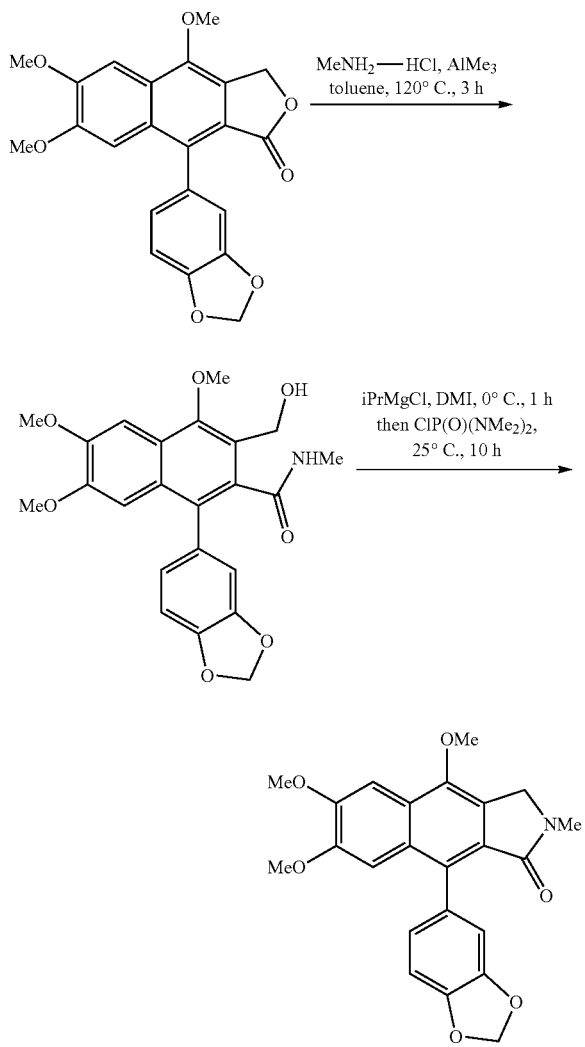

If the arylnaphthalene lignan compound is the compound of Chemical Formula 6, the preparation method according to the present disclosure may further include Schemes B, C and D sequentially following Scheme A:

[Scheme B]

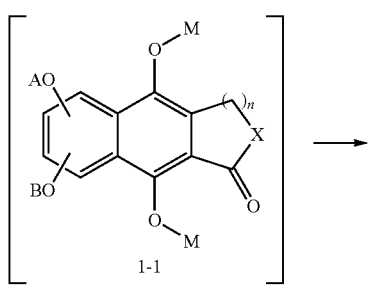

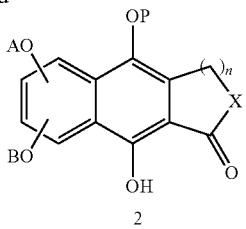

[Scheme C]

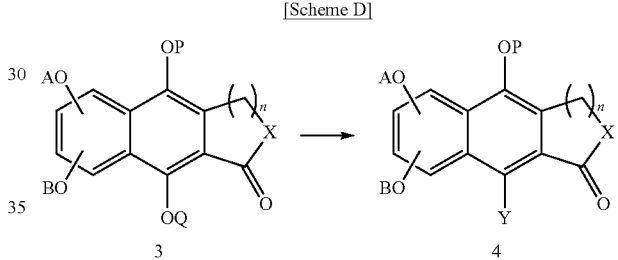

[Scheme D]

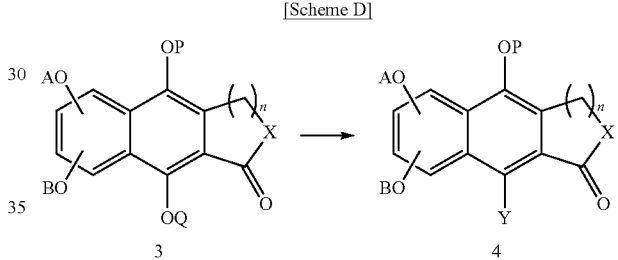

wherein
P is a protecting group of a hydroxyl group;
Q is sulfonyl; and
Scheme D is a Suzuki-Miyaura reaction.

In the present disclosure, the Suzuki-Miyaura reaction refers, for example, to a carbon-carbon cross-coupling reaction of an organoboron compound with an aryl halide catalyzed by a palladium catalyst (Miyaura, N.; Suzuki, A. Chem. Rev. 1995, 95, 2457.).

In Scheme B, the hydroxyl group at 4-position of the compound of Chemical Formula 1-1 is selectively protected. Any protecting group generally known in the art can be used to protect the hydroxyl group without limitation. The reaction of Scheme B is a one-pot reaction and the protecting group for selectively protecting the hydroxyl group may be an alkylether protecting group such as methyl, ethyl, t-butyl, benzyl, methoxymethyl, etc.; a silyl protecting group such as trimethylsilyl, t-butyldiphenylsilyl, t-butyldimethylsilyl, tri-isopropylsilyl, etc. or a carbonate protecting group such as t-butoxycarbonyl, methoxycarbonyl, ethoxycarbonyl. Specifically, the protecting group may be t-butoxycarbonyl. The reaction temperature of Scheme B may vary depending on the protecting group or the solvent used but may be specifically 25-40° C. The reaction time may also depending on the reaction temperature and the solutes used but may be specifically 1-24 hours.

In the preparation method according to the present disclosure, the reaction of Scheme C is a reaction for converting the phenolic hydroxyl group at the 9-position of the compound of Chemical Formula 2 to a pseudohalogen and includes a reaction of the compound of Chemical Formula 2 with a sulfonic anhydride. In the present disclosure, the sulfonic anhydride means an anhydride of a sulfonic acid and may have the general formula RS(=O)$_2$OS(=O)$_2$R. In the preparation method according to the present disclosure, the sulfonic anhydride may be one or more selected from a group consisting of trifluoromethansulfonic anhydride, methanesulfonic anhydride, pentafluoroethanesulfonic anhydride, p-toluenesulfonic anhydride and benzenesulfonic anhydride. The sulfonic anhydride may be replaced by a sulfonyl chloride such as trifluoromethanesulfonyl chloride, methanesulfonyl chloride, pentafluoroethanesulfonyl chloride, p-toluenesulfonyl chloride and benzenesulfonyl chloride.

In the preparation method according to the present disclosure, the sulfonate may be one or more selected from a group consisting of trifluoromethanesulfonate, methanesulfonate, pentafluoroethanesulfonate, p-toluenesulfonate and benzenesulfonate.

In the present disclosure, the sulfonyl group may be SO$_2$R$^{10}$, wherein R$^{10}$ is methyl, trifluoromethyl, methylphenyl or nitrophenyl.

In the preparation method according to the present disclosure, the sulfonic anhydride may be used in an amount of 1.0-3.0 equivalents, more specifically 1.2-1.5 equivalents, based on the compound Chemical Formula 2.

In Scheme C, chloroform, dichloromethane, triethylamine, pyridine, diisopropylethylamine, carbon tetrachloride, etc. may be used as a solvent, without being limited thereto. In Scheme C, the sulfonic anhydride may be used in an amount of 1.0-3.0 equivalents, more specifically 1.2-1.5 equivalents, based on the compound of Chemical Formula 2. A high yield can be achieved when the sulfonic anhydride is used with the above-described equivalents. The reaction temperature of Scheme C may vary depending on the protecting group or the solvent and may be specifically 25-40° C. The reaction time of Scheme C may vary depending on the reaction temperature and the solutes used but may be specifically 30 minutes to 10 hours.

Scheme D is a Suzuki-Miyaura reaction for introducing the substituent Y at the 9-position of the compound of Chemical Formula 4.

Scheme D may be carried out using a palladium catalyst. The catalyst may be selected adequately depending on the solutes and the solvent. Specifically, the palladium catalyst may be palladium(II) chloride, palladium(II) acetate, bis(triphenylphosphine)palladium(II) chloride, bis(dibenzylideneacetone)palladium(0), tetrakis(triphenylphosphine)palladium(0), [1,1'-bis(diphenylphosphino)-ferrocene]palladium(II) dichloride dichloromethane, etc., but is not limited thereto. The palladium catalyst may be specifically used in 0.01-1.0 equivalent.

A solvent used in Scheme D may be a protic polar solvent or a mixture of an anhydrous ether or an anhydrous aromatic hydrocarbon with water. Specifically, the protic polar solvent that can be used in Scheme D may be methanol, ethanol, propanol, isopropanol, butanol, etc., the anhydrous ether may be diethyl ether, tetrahydrofuran, dioxane, dimethoxyethane, etc. and the anhydrous aromatic hydrocarbon may be benzene, toluene, xylene, etc. More specifically, the solvent may be a mixture of an anhydrous ether with water or a mixture of tetrahydrofuran or dioxane with water. In the mixture solvent, a mixing proportion may be 1:1 to 20:1.

A ligand used in Scheme D may be selected appropriately depending on the solutes and the solvent. Specifically, triphenylphosphine, tricyclohexylphosphine, 2-dicyclohexylphosphino-2',6'-dimethoxybiphenyl, 2-dicyclohexylphosphino-2',6'-diisopropoxy-1,1'-biphenyl, 2-dicyclohexylphosphino-2',4',6'-triisopropylbiphenyl, etc. may be used, without being limited thereto. The ligand may be used in 0.02-2.0 equivalents.

A base used in Scheme D may be selected appropriately depending on the solutes and the solvent. Specifically, an alkali metal carbonate such as lithium carbonate, potassium carbonate, potassium bicarbonate, cesium carbonate, sodium carbonate, etc. may be used. In Scheme D, the base may be used in 1.0-5.0 equivalents.

In Scheme D, an organoboron compound such as an organoboric acid, an organoboric acid ester or a potassium organotrifluoroborate may be used in 1.0-3.0 equivalents, specifically 1.5-2.0 equivalents.

The reaction temperature of Scheme D may vary depending on the solvent used but may be specifically 60-120° C. The reaction time of Scheme D may also vary depending on the reaction temperature and the solvent used but may be specifically 1-24 hours.

The preparation method according to the present disclosure may further include Scheme E of deprotecting the protecting group of the hydroxyl group at 4-position of the compound of Chemical Formula 4 following Scheme D:

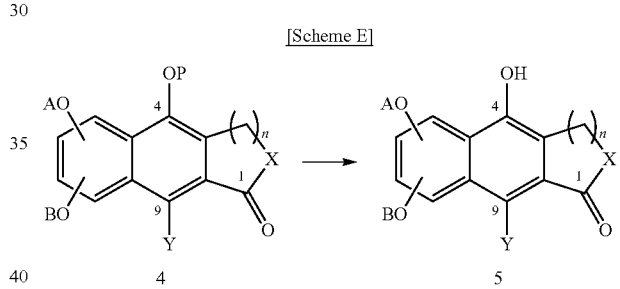

[Scheme E]

In Scheme E, the compound of Chemical Formula 5 may be obtained by removing the t-butoxycarbonyl protecting group of phenol from the compound of Chemical Formula 4.

The deprotection reaction of the t-butoxycarbonyl protecting group of phenol may be carried out in an alcohol solvent in the presence of an acid catalyst such as hydrochloric acid, camphorsulfonic acid, p-toluenesulfonic acid, etc. or at 25° C. using an amine such as piperidine, pyrrolidine, etc. Specifically, piperidine may be used. The piperidine may be used in 1.0-10 equivalents, specifically 5.0 equivalents.

In Scheme E, an organochlorine solvent such as chloroform, dichloromethane, carbon tetrachloride, etc. may be used. Specifically, dichloromethane may be used.

The reaction temperature and the reaction time may vary depending on the solutes and the solvent used. The reaction may be carried out at 0-40° C. for 1-10 hours, specifically at 25° C. for 5 hours.

The preparation method according to the present disclosure may further include Scheme F of converting the hydroxyl group of the compound of Chemical Formula 5 to Z following Scheme E:

[Scheme F]

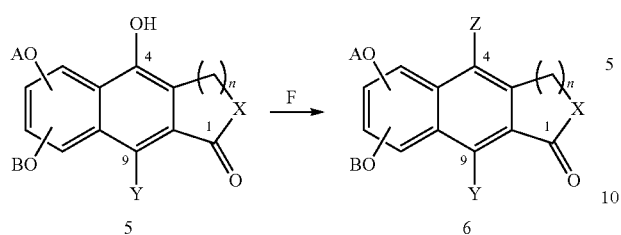

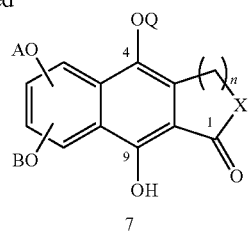

In Scheme F, to prepare the compound of Chemical Formula 6, the compound of Chemical Formula 5 may be reacted with a halogen compound in the presence of a base.

In Scheme F, an aprotic anhydrous polar solvent, an anhydrous ether solvent or an anhydrous aromatic hydrocarbon solvent may be used. Specifically, the aprotic anhydrous polar solvent may be N,N-dimethylformamide, N,N-dimethylacetamide, dimethyl sulfoxide, acetonitrile, acetone, carbon tetrachloride, chloroform, dichloromethane, etc. The anhydrous ether solvent may be diethyl ether, tetrahydrofuran, dioxane, dimethoxyethane, etc. And, the anhydrous aromatic hydrocarbon solvent may be benzene, toluene, xylene, etc. Specifically, an aprotic anhydrous polar solvent or an anhydrous ether solvent may be used and, more specifically, N,N-dimethylformamide, diethyl ether or tetrahydrofuran may be used.

The base that can be used in Scheme F may be selected adequately depending on the reaction solvent. Any weak or strong base may be used as long as the reaction is not negatively affected. For example, an alkali metal hydride such as sodium hydride, lithium hydride, etc., an alkaline earth metal hydride such as potassium hydride, etc., an alkali metal hydroxide such as sodium hydroxide, potassium hydroxide, etc. or an alkali metal carbonate such as lithium carbonate, potassium carbonate, potassium bicarbonate, etc. may be used. Most specifically, potassium carbonate may be used.

In Scheme F, the halogen compound may be used in 1.0-3.0 equivalents, specifically 1.2-1.5 equivalents. A good yield may be achieved when the halogen compound is used in the above-described amount. The reaction temperature of Scheme F may vary depending on the protecting group or the solvent used but may be 25-80° C. The reaction time may vary depending on the reaction temperature and the solutes used but may be 30 minutes to 12 hours. Specifically, the reaction may be carried out at 40° C. for 2 hours.

If the arylnaphthalene lignan compound is the compound of Chemical Formula 9, the preparation method according to the present disclosure may further include Schemes G, H and I sequentially following Scheme A:

[Scheme G]

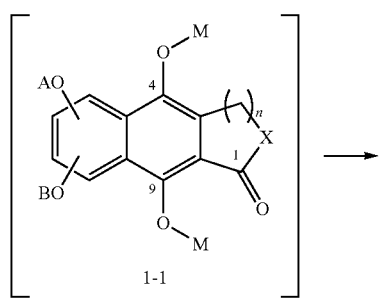

[Scheme H]

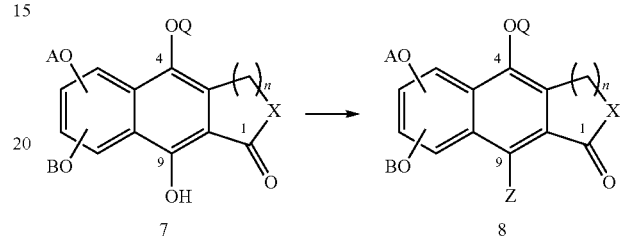

[Scheme I]

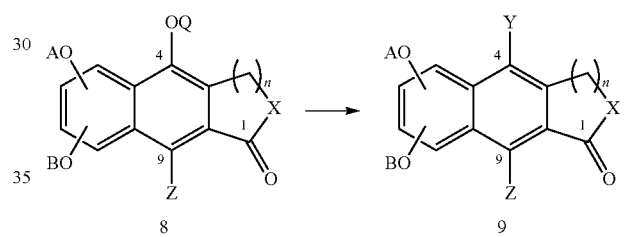

wherein

Q is sulfonyl; and

Scheme I is a Suzuki-Miyaura reaction.

In Scheme G, the hydroxyl group at 4-position of the compound 1-1 may be selectively protected. In Scheme G, diethyl ether or tetrahydrofuran may be used as a solvent, but without being limited thereto.

A base that can be used in Scheme G may be selected adequately depending on the reaction solvent. For example, lithium bis(trimethylsilyl)amide, potassium bis(trimethylsilyl)amide, sodium bis(trimethylsilyl)amide, lithium t-butoxide, potassium t-butoxide, sodium t-butoxide, lithium diisopropylamide, s-butyllithium, t-butyllithium, etc. may be used. Most specifically, lithium bis(trimethylsilyl)amide may be used.

In Scheme G, a sulfonic anhydride may be used in 1.0-3.0 equivalents, specifically 1.5-2.0 equivalents.

The reaction temperature of Scheme G may vary depending on the solutes used but may be −30 to −80° C. Specifically, the reaction may be carried out while raising temperature from −78° C. to −40° C. The reaction time may vary depending on the reaction temperature and the solutes used but may be 1-5 hours, specifically 2 hours.

Specifically, the reaction with the sulfonic anhydride may be carried out to selectively protect the phenolic hydroxyl group continuously without any purification process. The sulfonic anhydride may be used in 1.0-2.0 equivalents, specifically 1.0 equivalents. In Scheme G, the reaction temperature may vary depending on the solvent but may be 10-40° C. The reaction time may vary depending on the reaction temperature and the solvent used but may be 1-24 hours. Specifically, the reaction may be carried out at 25° C. for 12 hours.

In Scheme H, to prepare the Compound of Chemical Formula 8, the Compound of Chemical Formula 7 may be reacted with a halogen compound in the presence of a base.

In Scheme H, an aprotic anhydrous polar solvent, an anhydrous ether solvent or an anhydrous aromatic hydrocarbon solvent may be used. Specifically, the aprotic anhydrous polar solvent may be N,N-dimethylformamide, N,N-dimethylacetamide, dimethyl sulf oxide, acetonitrile, acetone, carbon tetrachloride, chloroform, dichloromethane, etc. The anhydrous ether may be diethyl ether, tetrahydrofuran, dioxane, dimethoxyethane, etc. And, the anhydrous aromatic hydrocarbon solvent may be benzene, toluene, xylene, etc. Specifically, an aprotic anhydrous polar solvent or an anhydrous ether solvent may be used. More specifically, N,N-dimethylformamide, diethyl ether or tetrahydrofuran may be used.

The base that can be used in Scheme H may be selected adequately depending on the reaction solvent. Any weak or strong base may be used as long as the reaction is not negatively affected. For example, an alkali metal hydride such as sodium hydride, lithium hydride, etc., an alkaline earth metal hydride such as potassium hydride, etc., an alkali metal hydroxide such as sodium hydroxide, potassium hydroxide, etc. or an alkali metal carbonate such as lithium carbonate, potassium carbonate, potassium bicarbonate, etc. may be used. Most specifically, potassium carbonate may be used.

In Scheme H, the halogen compound may be used in 1.0-3.0 equivalents, specifically 1.2-1.5 equivalents. A good yield can be achieved when the halogen compound is used in the above-described amount. The reaction temperature of Scheme F may vary depending on the protecting group or the solvent but may be 25-80° C. The reaction time may vary depending on the reaction temperature and the solutes used but may be 30 minutes to 12 hours. Specifically, the reaction may be carried out at 40° C. for 2 hours.

Scheme I may be a Suzuki-Miyaura reaction.

In Scheme I, a protic polar solvent or a mixture of an anhydrous ether or an anhydrous aromatic hydrocarbon with water may be used as a solvent. The protic polar solvent that can be used in the reaction may be methanol, ethanol, propanol, isopropanol, butanol, etc. The anhydrous ether that can be used in the reaction may be diethyl ether, tetrahydrofuran, dioxane, dimethoxyethane, etc. The anhydrous aromatic hydrocarbon solvent that can be used in the reaction may be benzene, toluene, xylene, etc. Specifically, a mixture of an anhydrous ether with water may be used. More specifically, a mixture of tetrahydrofuran or dioxane with water may be used. A mixing proportion may be from 1:1 to 20:1, most specifically 10:1.

A palladium catalyst used in Scheme I may be selected adequately depending on the solutes and the solvent. Palladium(II) chloride, palladium(II) acetate, bis(triphenylphosphine)palladium(II) chloride, bis(dibenzylideneacetone)palladium(0), tetrakis(triphenylphosphine)palladium(0), [1,1'-bis(diphenylphosphino)-ferrocene]palladium(II) dichloride dichloromethane, etc. may be used. Most specifically, palladium(II) acetate may be used. The palladium catalyst may be used in 0.01-1.0 equivalent, specifically 0.1 equivalent.

A ligand used in Scheme I may be selected adequately depending on the solutes and the solvent. Triphenylphosphine, tricyclohexylphosphine, 2-dicyclohexylphosphino-2',6'-dimethoxybiphenyl, 2-dicyclohexylphosphino-2',6'-diisopropoxy-1,1'-biphenyl, 2-dicyclohexylphosphino-2',4',6'-triisopropylbiphenyl, etc. may be used. Most specifically, tricyclohexylphosphine may be used. The ligand may be used in 0.02-2.0 equivalents, specifically 0.2 equivalent.

A base used in Scheme I may be selected adequately depending on the solutes and the solvent. An alkali metal carbonate such as lithium carbonate, potassium carbonate, potassium bicarbonate, cesium carbonate, sodium carbonate, etc. may be used. Most specifically, cesium carbonate may be used. The base may be used in 1.0-5.0 equivalents, specifically 3.0 equivalents.

In Scheme I, a potassium aryltrifluoroborate may be used in 1.0-3.0 equivalents, specifically 1.5-2.0 equivalents.

The reaction temperature of Scheme I may vary depending on the solvent but may be 60-120° C., specifically 80° C. The reaction time may vary depending on the reaction temperature and the solvent used but may be 1-24 hours, specifically 12 hours.

MODE FOR INVENTION

Hereinafter, the present disclosure will be described in detail through examples. However, the following examples are for illustrative purposes only and it will be apparent to those of ordinary skill in the art that the scope of the present disclosure is not limited by the examples.

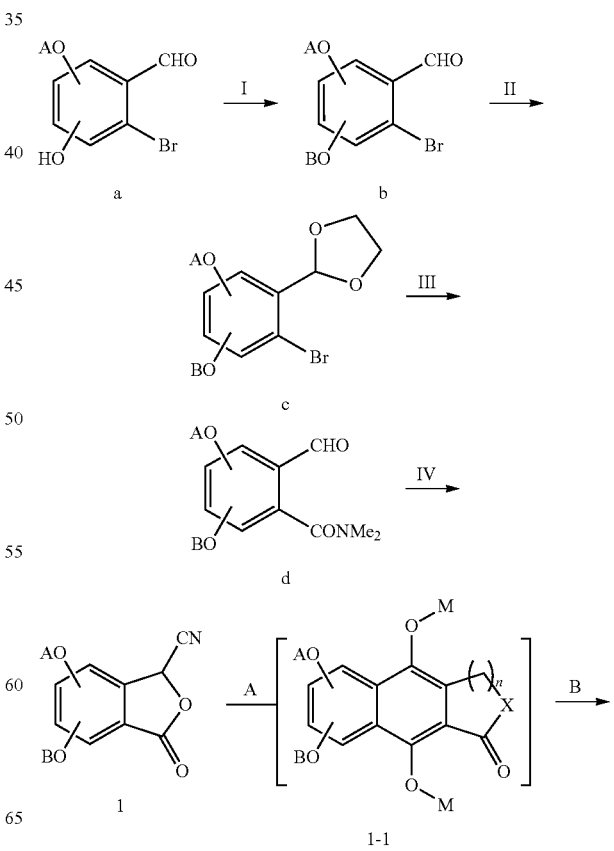

-continued

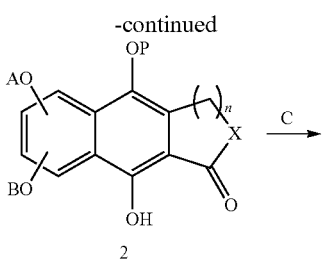
2

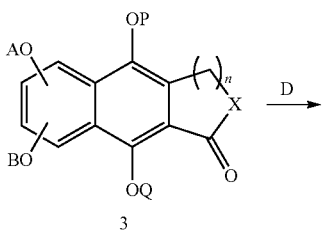
3

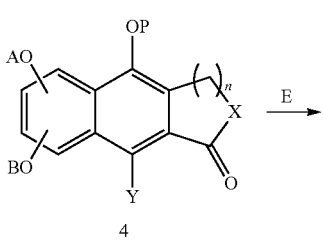
4

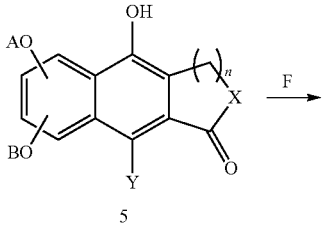
5

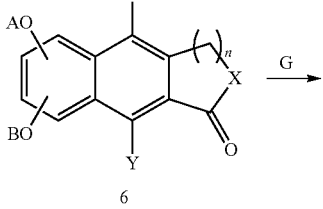
6

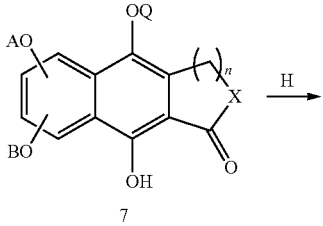
7

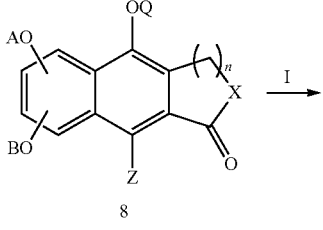
8

-continued

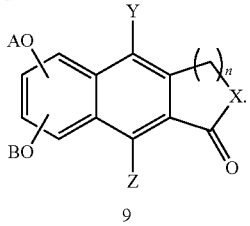
9

EXAMPLE 1

Synthesis of 9-(benzo[d][1,3]dioxol-5-yl)-4,6,7-trimethoxynaphtho[2,3-c]furan-1(3H)-one (justicidin A)

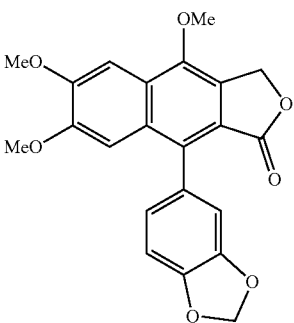 [SMILES: COc1cc2c(OC)c3c(c(-c4ccc5c(c4)OCO5)c2cc1OC)C(=O)OC3]

EXAMPLE 1-1

Synthesis of 2-(2-bromo-4,5-dimethoxyphenyl)-1,3-dioxolane [Scheme II]

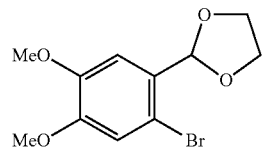 [SMILES: COc1cc(Br)c(C2OCCO2)cc1OC]

EXAMPLE 1-1

Synthesis of 5 g of 2-bromo-4,5-dimethoxybenzaldehyde (20.5 mmol) was dissolved in 205 mL of benzene (0.1 M) and 195 mg of p-toluenesulfonic acid hydrate (1.0 mmol) and 3.82 g of ethylene glycol (61.5 mmol) were sequentially added at 0° C. After connecting with a Dean-Stark trap and increasing reaction temperature to 90° C., the mixture was reacted for 5 hours. After terminating the reaction by adding 100 mL of sodium bicarbonate aqueous solution, followed by extraction with EtOAc (3×50 mL), the organic layer was washed with brine (2×20 mL), dried with anhydrous Na2SO4, filtered and then concentrated. The remainder was purified by silica gel column chromatography to obtain 2.73 g of the target compound 2-(2-bromo-4,5-dimethoxyphenyl)-1,3-dioxolane (20.3 mmol, 99%). 2-(2-bromo-4,5-dimethoxyphenyl)-1,3-dioxolane [Scheme II]

$^1$H NMR (400 MHz, CDCl$_3$) ⊚7.11 (s, 1H), 7.02 (s, 1H), 6.00 (s, 2H), 4.20-4.16 (m, 2H), 4.11-4.05 (m, 2H), 3.89 (s, 3H), 3.88 (s, 3H).

EXAMPLE 1-2

Synthesis of 2-formyl-4,5-dimethoxy-N,N-dimethylbenzamide [Scheme III]

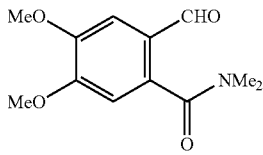 [SMILES: COc1cc(C=O)c(C(=O)N(C)C)cc1OC]

5 g of 2-(2-bromo-4,5-dimethoxyphenyl)-1,3-dioxolane (17.4 mmol) was dissolved in 174 mL of tetrahydrofuran (0.1 M) under nitrogen atmosphere and 22.6 mL of 1.0 M n-butyllithium (22.6 mmol) was added at −78° C. After carrying out reaction at the same temperature for 30 minutes, 2.25 g of N,N-dimethylcarbamoyl chloride (20.9 mmol) was added. After slowly increasing reaction temperature to 25° C., reaction was carried out for 5 hours. After lowering temperature again to 0° C., 0.87 mL of 0.5 N HCl aqueous solution was added. After carrying out reaction at the same temperature for 1 hour, the reaction was terminated by adding 100 mL of ammonium chloride aqueous solution. After extracting with EtOAc (3×50 mL), the organic layer was washed with brine (2×20 mL), dried with anhydrous Na2SO4, filtered and then concentrated. The remainder was purified by silica gel column chromatography to obtain 3.26 g of the target compound 2-formyl-4,5-dimethoxy-N,N-dimethylbenzamide (13.7 mmol, 79%).

$^1$H NMR (400 MHz, CDCl$_3$) ⊚9.90 (s, 1H), 7.43 (s, 1H), 6.84 (s, 1H), 4.00 (s, 3H), 3.99 (s, 3H), 3.18 (s, 3H), 2.86 (s, 3H).

EXAMPLE 1-3

Synthesis of 5,6-dimethoxy-3-oxo-1,3-dihydroisobenzofuran-1-carbonitrile [Scheme IV]

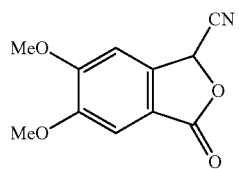 [SMILES: COc1cc2c(cc1OC)C(C#N)OC2=O]

2 g of 2-formyl-4,5-dimethoxy-N,N-dimethylbenzamide (8.44 mmol) was dissolved in 16.9 mL of dichloromethane (0.5 M) under nitrogen atmosphere and 165 mg of potassium cyanide (KCN) (2.53 mmol) and 669 mg of 18-crown-6 (2.53 mmol) were sequentially added at 0° C. After carrying out reaction at 25° C. for 30 minutes, 1.67 g of trimethylsilyl cyanide (16.9 mmol) was added and reaction was carried out at 25° C. for 5 hours. After removing the organic solvent under reduced pressure, 16.9 mL of acetic acid was added and reaction was carried out at 25° C. for 12 hours. After terminating the reaction by adding 20 mL of sodium bicarbonate aqueous solution, followed by extracting with EtOAc (3×10 mL), the organic layer was washed with brine (2×5 mL), dried with anhydrous Na2SO4, filtered and then concentrated. The remainder was purified by silica gel column chromatography to obtain 1.72 g of the target compound 5,6-dimethoxy-3-oxo-1,3-dihydroisobenzofuran-1-carbonitrile (7.85 mmol, 93%).

$^1$H NMR (400 MHz, CDCl$_3$) ⊚7.33 (s, 1H), 7.06 (s, 1H), 5.98 (s, 1H), 4.04 (s, 3H), 3.98 (s, 3H).

EXAMPLE 1-4

Synthesis of t-butyl 9-hydroxy-6,7-dimethoxy-1-oxo-1,3-dihydronaphtho[2,3-c]furan-4-yl carbonate [Scheme A+Scheme B]

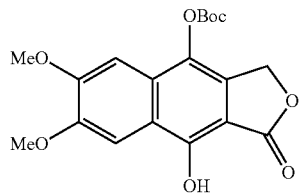

860 mg of 5,6-dimethoxy-3-oxo-1,3-dihydroisobenzofuran-1-carbonitrile (3.93 mmol) was dissolved in 98.2 mL of tetrahydrofuran (0.04 M) under nitrogen atmosphere and 11.8 mL of 1.0 M lithium bis(trimethylsilyl)amide (11.8 mmol) was added at −78° C. After carrying out reaction at −78° C. for 30 minutes, followed by increasing temperature to −40° C., 661 mg of 2(5H)-furanone (7.86 mmol) was added and reaction was carried out at the same temperature for 30 hours. After adding 858 mg of t-butoxycarbonyl carbonate (Boc2O) (3.93 mmol), reaction was carried out at 25° C. for 12 hours. After terminating the reaction by adding 80 mL of ammonium chloride aqueous, followed by extracting with EtOAc (3×30 mL), the organic layer was washed with brine (2×20 mL), dried with anhydrous Na2SO4, filtered and then concentrated. The remainder was purified by silica gel column chromatography to obtain 1.06 g of the target compound t-butyl 9-hydroxy-6,7-dimethoxy-1-oxo-1,3-dihydronaphtho[2,3-c]furan-4-yl carbonate (2.83 mmol, 72%).

$^1$H NMR (400 MHz, CDCl$_3$) ⊚8.39 (bs, 1H), 7.53 (s, 1H), 7.13 (s, 1H), 5.35 (s, 2H), 4.04 (s, 3H), 4.03 (s, 3H), 1.59 (s, 3H).

EXAMPLE 1-5

Synthesis of 9-(t-butoxycarbonyloxy)-6,7-dimethoxy-3-oxo-1,3-dihydronaphtho[2,3-c]furan-4-yl trifluoromethanesulfonate [Scheme C]

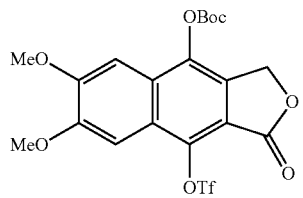

250 mg of t-butyl 9-hydroxy-6,7-dimethoxy-1-oxo-1,3-dihydronaphtho[2,3-c]furan-4-yl carbonate (0.665 mmol) was dissolved in 13.3 mL of dichloromethane (0.05 M) under nitrogen atmosphere and 78.9 mg of pyridine (0.998 mmol) and 225 mg of trifluoromethanesulfonic anhydride (Tf2O) (0.798 mmol) were sequentially added at 0° C. After increasing reaction temperature to 25° C., reaction was carried out for 2 hours. After terminating the reaction by adding 10 mL of sodium bicarbonate aqueous solution, followed by extracting with EtOAc (3×8 mL), the organic layer was washed with brine (2×4 mL), dried with anhydrous Na2SO4, filtered and then concentrated. The remainder was purified by silica gel column chromatography to obtain 334 mg of the target compound 9-(t-butoxycarbonyloxy)-6,7-dimethoxy-3-oxo-1,3-dihydronaphtho[2,3-c]furan-4-yl trifluoromethanesulfonate (0.658 mmol, 99%).

$^1$H NMR (400 MHz, CDCl$_3$) ⊙7.47 (s, 1H), 7.24 (s, 1H), 5.37 (s, 2H), 4.08 (s, 3H), 4.06 (s, 3H), 1.62 (s, 9H).

EXAMPLE 1-6

Synthesis of 9-(benzo[d][1,3]dioxol-5-yl)-6,7-dimethoxy-1-oxo-1,3-dihydronaphtho[2,3-c]furan-4-yl t-butylcarbonate [Scheme D]

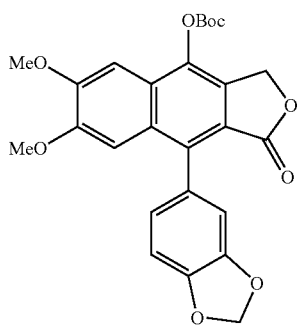

50.0 mg of 9-(t-butoxycarbonyloxy)-6, 7-dimethoxy-3-oxo-1,3-dihydronaphtho[2,3-c]furan-4-yl trifluoromethanesulfonate (0.098 mmol) was dissolved in 3.9 mL of 10:1 mixture solvent of dioxane and water (0.025 M) and 44.7 mg of potassium benzo[d][1,3]dioxol-5-yltrifluoroborate (0.196 mmol), 2.2 mg of palladium(II) acetate (Pd(OAc)2) (0.010 mmol), 5.6 mg of tricyclohexylphosphine (PCy3) (0.020 mmol) and 95.8 mg of cesium carbonate (Cs2CO3) (0.294 mmol) were sequentially added. After increasing reaction temperature to 80° C., reaction was carried out for 17 hours. After terminating the reaction by adding 3 mL of ammonium chloride aqueous solution, followed by extracting with EtOAc (3×2 mL), the organic layer was washed with brine (2×2 mL), dried with anhydrous Na2SO4, filtered and then concentrated. The remainder was purified by silica gel column chromatography to obtain 46.1 mg of the target compound 9-(benzo[d][1,3]dioxol-5-yl)-6,7-dimethoxy-1-oxo-1,3-dihydronaphtho[2,3-c]furan-4-yl t-butylcarbonate (0.096 mmol, 98%).

$^1$H NMR (400 MHz, CDCl$_3$) ⊙7.25 (s, 1H), 7.12 (s, 1H), 6.97 (d, 1H, J=8.0 Hz), 6.85 (s, 1H), 6.83 (d, 1H, J=7.6 Hz), 6.08 (d, 2H, J=16.4 Hz), 5.33 (s, 2H), 4.06 (s, 3H), 3.81 (s, 3H) 1.63 (s, 9H).

EXAMPLE 1-7

Synthesis of 9-(benzo[d][1,3]dioxol-5-yl)-4-hydroxy-6,7-dimethoxynaphtho[2,3-c]furan-1(3H)-one (diphyllin) [Scheme E]

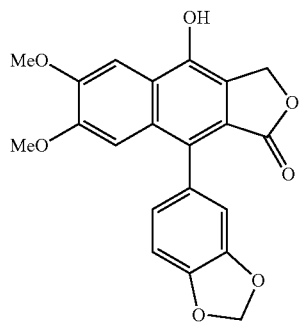 [SMILES: COc1cc2c(O)c3c(c(-c4ccc5c(c4)OCO5)c2cc1OC)C(=O)OC3]

30.4 mg of 9-(benzo[d][1,3]dioxol-5-yl)-6,7-dimethoxy-1-oxo-1,3-dihydronaphtho[2,3-c]furan-4-yl t-butylcarbonate (0.063 mmol) was dissolved in 0.32 mL of dichloromethane (0.2 M) and 10.8 mg of piperidine (0.127 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 21.2 mg of the target compound 9-(benzo[d][1,3]dioxol-5-yl)-4-hydroxy-6,7-dimethoxynaphtho[2,3-c]furan-1(3H)-one (diphyllin) (0.056 mmol, 88%).

$^1$H NMR (400 MHz, DMSO-d$_6$) ⊙10.39 (s, 1H), 7.62 (s, 1H), 7.01 (d, 1H, J=8.0 Hz), 6.95 (s, 1H), 6.68 (d, 1H, J=1.6 Hz), 6.75 (dd, 1H, J=1.6, 7.6 Hz), 6.11 (s, 2H), 5.36 (s, 2H), 3.94 (s, 3H), 3.65 (s, 3H).

EXAMPLE 1-8

Synthesis of 9-(benzo[d][1,3]dioxol-5-yl)-4,6,7-trimethoxynaphtho[2,3-c]furan-1(3H)-one (justicidin A) [Scheme F]

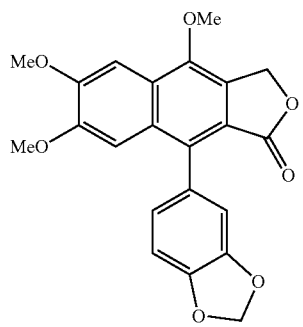 [SMILES: COc1cc2c(OC)c3c(c(-c4ccc5c(c4)OCO5)c2cc1OC)C(=O)OC3]

10.2 mg of 9-(benzo[d][1,3]dioxol-5-yl)-4-hydroxy-6,7-dimethoxynaphtho[2,3-c]furan-1(3H)-one (diphyllin) (0.027 mmol) was dissolved in 0.27 mL of N,N-dimethylformamide (0.1 M) and 5.7 mg of iodomethane (MeI) (0.040 mmol) and 7.4 mg of potassium carbonate (K2CO3) (0.054 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL, the organic layer was washed with brine (2×1 mL), dried with anhydrous Na2SO4, filtered and then concentrated. The remainder was purified by silica gel column chromatography to obtain 9.3 mg of the target compound 9-(benzo[d][1,3]dioxol-5-yl)-4,6,7-trimethoxynaphtho[2,3-c]furan-1(3H)-one (justicidin A) (0.024 mmol, 88%).

$^1$H NMR (400 MHz, CDCl$_3$) ⊚7.55 (s, 1H), 7.06 (s, 1H), 6.96 (d, 1H, J=8.0 Hz), 6.83 (d, 1H, J=1.6 Hz), 6.80 (dd, 1H, J=1.6, 8.0 Hz), 6.10 (d, 1H, J=1.2 Hz), 6.05 (d, 1H, J=1.2 Hz), 4.14 (s, 3H), 4.08 (s, 3H), 3.81 (s, 3H).

EXAMPLE 2

Synthesis of 9-(3,4-dimethoxyphenyl)-4,6,7-trimethoxynaphtho[2,3-c]furan-1(3H)-one (cilinaphthalide B)

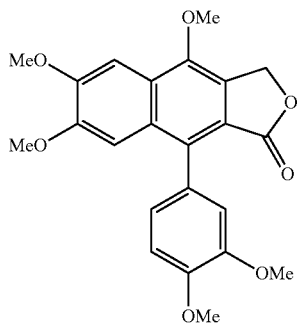 [SMILES: COc1ccc(-c2c3c(c(OC)c4cc(OC)c(OC)cc24)COC3=O)cc1OC]

EXAMPLE 2-1

Synthesis of t-butyl 9-(3,4-dimethoxyphenyl)-6,7-dimethoxy-1-oxo-1,3-dihydronaphtho[2,3-c]furan-4-yl carbonate [Scheme D]

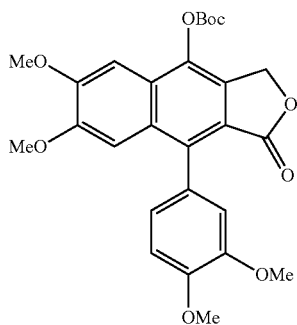

44.2 mg of the target compound t-butyl 9-(3,4-dimethoxyphenyl)-6,7-dimethoxy-1-oxo-1,3-dihydronaphtho[2,3-c]furan-4-yl carbonate (0.089 mmol, 91%) was obtained in the same manner as in Example 1-6 from the 9-(t-butoxycarbonyloxy)-6,7-dimethoxy-3-oxo-1,3-dihydronaphtho[2,3-c]furan-4-yl trifluoromethanesulfonate prepared in Example 1-5, except for using 47.8 mg of potassium 3,4-dimethoxyphenyltrifluoroborate (0.052 mmol) instead of potassium benzo[d][1,3]dioxol-5-yltrifluoroborate.

$^1$H NMR (400 MHz, CDCl$_3$) ⊚7.26 (s, 1H), 7.16 (s, 1H), 7.06 (d, 1H, J=8.4 Hz), 6.98 (dd, 1H, J=1.6, 8.0 Hz), 6.92 (d, 1H, J=1.6 Hz), 5.36 (s, 2H), 4.08 (s, 3H), 4.01 (s, 3H), 3.89 (s, 3H), 3.80 (s, 3H), 1.66 (s, 9H).

EXAMPLE 2-2

Synthesis of 9-(3,4-dimethoxyphenyl)-4-hydroxy-6,7-dimethoxynaphtho[2,3-c]furan-1(3H)-one [Scheme E]

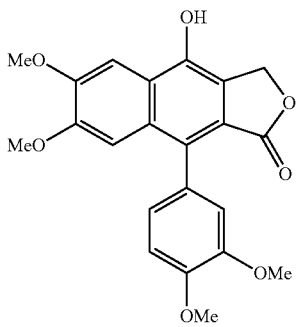 [SMILES: COc1ccc(-c2c3c(c(O)c4cc(OC)c(OC)cc24)COC3=O)cc1OC]

32.3 mg of t-butyl 9-(3,4-dimethoxyphenyl)-6,7-dimethoxy-1-oxo-1,3-dihydronaphtho[2,3-c]furan-4-yl carbonate (0.065 mmol) was dissolved in 0.33 mL of dichloromethane (0.2 M) and 11.1 mg of piperidine (0.130 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 23.2 mg of the target compound 9-(3,4-dimethoxyphenyl)-4-hydroxy-6,7-dimethoxynaphtho[2,3-c]furan-1(3H)-one (0.059 mmol, 90%).

$^1$H NMR (400 MHz, DMSO-d$_6$) ⊚10.36 (s, 1H), 7.63 (s, 1H), 7.05 (d, 1H, J=8.0 Hz), 7.02 (s, 1H), 6.89 (d, 1H, J=1.6 Hz), 6.85 (dd, 1H, J=1.6, 8.0 Hz), 5.36 (s, 2H), 3.94 (s, 3H), 3.84 (s, 3H), 3.72 (s, 3H), 3.64 (s, 3H).

EXAMPLE 2-3

Synthesis of 9-(3,4-dimethoxyphenyl)-4,6,7-trimethoxynaphtho[2,3-c]furan-1(3H)-one (cilinaphthalide B) [Scheme F]

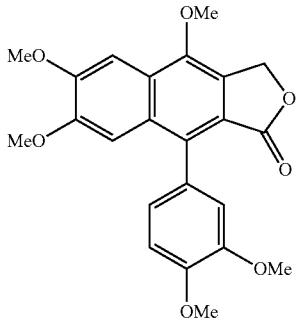 [SMILES: COc1ccc(-c2c3c(c(OC)c4cc(OC)c(OC)cc24)COC3=O)cc1OC]

11.3 mg of 9-(3,4-dimethoxyphenyl)-4-hydroxy-6,7-dimethoxynaphtho[2,3-c]furan-1(3H)-one (0.029 mmol) was dissolved in 0.29 mL of N,N-dimethylformamide (0.1 M) and 6.1 mg of iodomethane (MeI) (0.043 mmol) and 7.9 mg of potassium carbonate (K2CO3) (0.057 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 11.3 mg of the target compound 9-(3,4-dimethoxyphenyl)-4,6,7-trimethoxynaphtho[2,3-c]furan-1(3H)-one (cilinaphthalide B) (0.028 mmol, 97%).

$^1$H NMR (400 MHz, CDCl$_3$) ⊙7.55 (s, 1H), 7.09 (s, 1H), 7.30 (d, 1H, J=8.0 Hz), 6.98-6.89 (m, 2H), 5.55 (s, 2H), 4.14 (s, 3H), 4.08 (s, 3H), 3.98 (s, 3H), 3.87 (s, 3H), 3.78 (s, 3H).

EXAMPLE 3

Synthesis of 9-(3,5-dimethoxyphenyl)-4,6,7-trimethoxynaphtho[2,3-c]furan-1(3H)-one

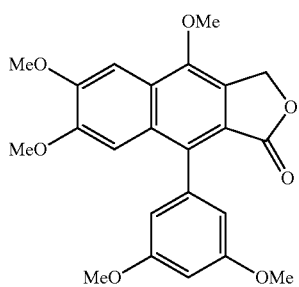 [SMILES: COc1cc(OC)cc(-c2c3c(c(OC)c4cc(OC)c(OC)cc24)COC3=O)c1]

EXAMPLE 3-1

Synthesis of t-butyl 9-(3,5-dimethoxyphenyl)-6,7-dimethoxy-1-oxo-1,3-dihydronaphtho[2,3-c]furan-4-yl carbonate [Scheme D]

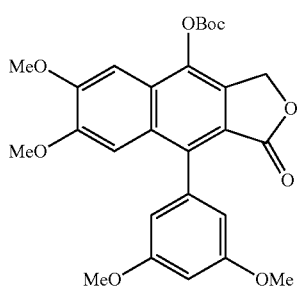

45.7 mg of the target compound t-butyl 9-(3,5-dimethoxyphenyl)-6,7-dimethoxy-1-oxo-1,3-dihydronaphtho[2,3-c]furan-4-yl carbonate (0.092 mmol, 94%) was obtained in the same manner as in Example 1-6 from the 9-(t-butoxycarbonyloxy)-6,7-dimethoxy-3-oxo-1,3-dihydronaphtho[2,3-c]furan-4-yl trifluoromethanesulfonate prepared in Example 1-5, except for using 47.8 mg of potassium 3,5-dimethoxyphenyltrifluoroborate (0.052 mmol) instead of potassium benzo[d][1,3]dioxol-5-yltrifluoroborate.

$^1$H NMR (400 MHz, CDCl$_3$) ⊙7.25 (s, 1H), 7.12 (s, 1H), 6.60 (t, 1H, J=2.4 Hz), 6.52 (d, 2H, J=2.4 Hz), 5.34 (s, 2H), 4.06 (s, 3H), 3.82 (s, 6H), 3.80 (s, 3H), 1.64 (s, 9H).

EXAMPLE 3-2

Synthesis of 9-(3,5-dimethoxyphenyl)-4-hydroxy-6,7-dimethoxynaphtho[2,3-c]furan-1(3H)-one [Scheme E]

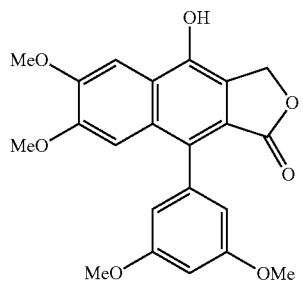 [SMILES: COc1cc(OC)cc(-c2c3c(c(O)c4cc(OC)c(OC)cc24)COC3=O)c1]

33.2 mg of t-butyl 9-(3,5-dimethoxyphenyl)-6,7-dimethoxy-1-oxo-1,3-dihydronaphtho[2,3-c]furan-4-yl carbonate (0.067 mmol) was dissolved in 0.33 mL of dichloromethane (0.2 M) and 11.4 mg of piperidine (0.134 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na$_2$SO$_4$, filtered and then concentrated. The remainder was purified by silica gel column chromatography to obtain 22.3 mg of the target compound 9-(3,5-dimethoxyphenyl)-4-hydroxy-6,7-dimethoxynaphtho[2,3-c]furan-1(3H)-one (0.056 mmol, 84%).

$^1$H NMR (400 MHz, DMSO-d$_6$) ⊙10.45 (s, 1H), 7.62 (s, 1H), 6.96 (s, 1H), 6.58 (s, 1H), 6.45 (d, 2H, J=1.2 Hz), 5.36 (s, 2H), 3.94 (s, 3H), 3.76 (s, 6H), 3.64 (s, 3H).

EXAMPLE 3-3

Synthesis of 9-(3,5-dimethoxyphenyl)-4,6,7-trimethoxynaphtho[2,3-c]furan-1(3H)-one [Scheme F]

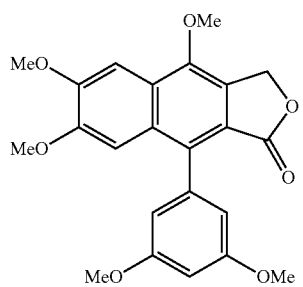 [SMILES: COc1cc(OC)cc(-c2c3c(c(OC)c4cc(OC)c(OC)cc24)COC3=O)c1]

10.5 mg of 9-(3,5-dimethoxyphenyl)-4-hydroxy-6,7-dimethoxynaphtho[2,3-c]furan-1(3H)-one (0.027 mmol) was dissolved in 0.27 mL of N,N-dimethylformamide (0.1 M) and 5.6 mg of iodomethane (MeI) (0.040 mmol) and 7.3 mg of potassium carbonate (K2CO3) (0.053 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 10.7 mg of the target compound 9-(3,5-dimethoxyphenyl)-4,6,7-trimethoxynaphtho[2,3-c]furan-1(3H)-one (cilinaphthalide B) (0.026 mmol, 99%).

1H NMR (400 MHz, CDCl3) δ 7.54 (s, 1H), 7.07 (s, 1H), 6.58 (t, 1H, J=2.4 Hz), 6.50 (d, 2H, J=2.4 Hz), 5.55 (s, 2H), 4.14 (s, 3H), 4.07 (s, 3H), 3.81 (s, 6H), 3.79 (s, 3H).

EXAMPLE 4

Synthesis of 4,6,7-trimethoxy-9-(4-methoxyphenyl)naphtho[2,3-c]furan-1(3H)-one

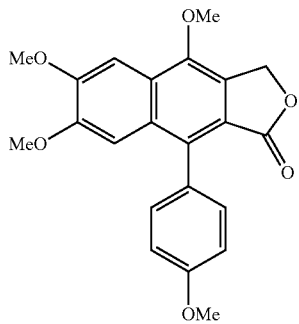 [SMILES: COc1ccc(-c2c3c(c(OC)c4cc(OC)c(OC)cc24)COC3=O)cc1]

EXAMPLE 4-1

Synthesis of t-butyl 6,7-dimethoxy-9-(4-methoxyphenyl)-1-oxo-1,3-dihydronaphtho[2,3-c]furan-4-yl carbonate [Scheme D]

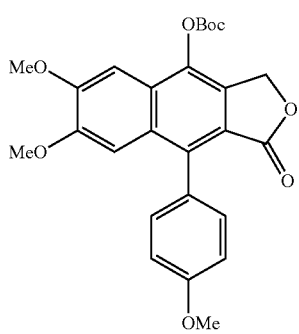

36.5 mg of the target compound t-butyl 6,7-dimethoxy-9-(4-methoxyphenyl)-1-oxo-1,3-dihydronaphtho[2,3-c]furan-4-yl carbonate (0.078 mmol, 80%) was obtained in the same manner as in Example 1-6 from the 9-(t-butoxycarbonyloxy)-6,7-dimethoxy-3-oxo-1,3-dihydronaphtho[2,3-c]furan-4-yl trifluoromethanesulfonate prepared in Example 1-5, except for using 41.9 mg of potassium 4-methoxyphenyltrifluoroborate (0.052 mmol) instead of potassium benzo[d][1,3]dioxol-5-yltrifluoroborate.

1H NMR (400 MHz, CDCl3) ⊚7.31 (d, 2H, J=8.4 Hz), 7.25 (s, 1H), 7.12 (s, 1H), 7.06 (d, 2H, J=8.8 Hz), 5.34 (s, 2H), 4.06 (s, 3H), 3.91 (s, 3H), 3.78(s, 3H), 1.63 (s, 9H).

EXAMPLE 4-2

Synthesis of 4-hydroxy-6,7-dimethoxy-9-(4-methoxyphenyl)naphtho[2,3-c]furan-1(3H)-one [Scheme E]

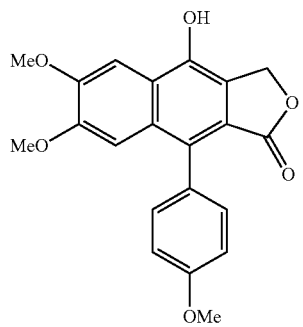 [SMILES: COc1ccc(-c2c3c(c(O)c4cc(OC)c(OC)cc24)COC3=O)cc1]

23.5 mg of t-butyl 9-(3,5-dimethoxyphenyl)-4-methoxy-1-oxo-1,3-dihydronaphtho[2,3-c]furan-4-yl carbonate (0.050 mmol) was dissolved in 0.25 mL of dichloromethane (0.2 M) and 8.6 mg of piperidine (0.101 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 12.7 mg of the target compound 4-hydroxy-6,7-dimethoxy-9-(4-methoxyphenyl)naphtho[2,3-c]furan-1(3H)-one (0.035 mmol, 69%).

1H NMR (400 MHz, DMSO-d6) ⊚10.4 (s, 1H), 7.62 (s, 1H), 7.23 (d, 2H, J=8.0 Hz), 7.03 (d, 2H, J=8.4 Hz), 6.94 (s, 1H), 5.36 (s, 2H), 3.94 (s, 3H), 3.84 (s, 3H), 3.62 (s, 3H).

EXAMPLE 4-3

Synthesis of 4,6,7-trimethoxy-9-(4-methoxyphenyl)naphtho[2,3-c]furan-1(3H)-one [Scheme F]

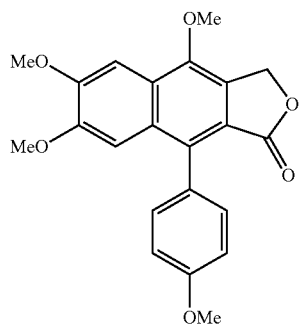 [SMILES: COc1ccc(-c2c3c(c(OC)c4cc(OC)c(OC)cc24)COC3=O)cc1]

5.0 mg of 9-(4-methoxyphenyl)-4-hydroxy-6,7-dimethoxynaphtho[2,3-c]furan-1(3H)-one (0.014 mmol) was dissolved in 0.14 mL of N,N-dimethylformamide (0.1 M) and 2.9 mg of iodomethane (MeI) (0.020 mmol) and 3.8 mg of potassium carbonate (K2CO3) (0.027 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 5.0 mg of the target compound 9-(4-methoxyphenyl)-4,6,7-trimethoxynaphtho[2,3-c]furan-1(3H)-one (cilinaphthalide B) (0.013 mmol, 97%).

$^1$H NMR (400 MHz, CDCl$_3$) ⊚7.55 (s, 1H), 7.28 (d, 2H, J=8.8 Hz), 7.06 (s, 1H), 7.05 (d, 2H, J=8.8 Hz), 5.54 (s, 2H), 4.13 (s, 3H), 4.07 (s, 3H), 3.90 (s, 3H), 3.78 (s, 3H).

EXAMPLE 5

Synthesis of 4,6,7-trimethoxy-9-phenylnaphtho[2,3-c]furan-1(3H)-one

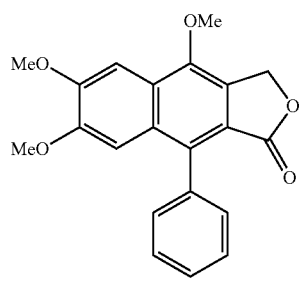 [SMILES: COc1cc2c(OC)c3c(c(-c4ccccc4)c2cc1OC)C(=O)OC3]

EXAMPLE 5-1

Synthesis of t-butyl 6,7-dimethoxy-1-oxo-9-phenyl-1,3-dihydronaphtho[2,3-c]furan-4-yl carbonate [Scheme D]

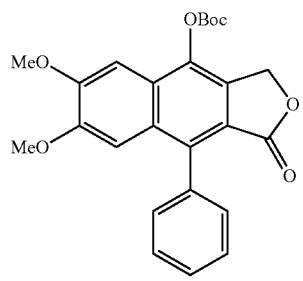

34.6 mg of the target compound t-butyl 6,7-dimethoxy-1-oxo-9-phenyl-1,3-dihydronaphtho[2,3-c]furan-4-yl carbonate (0.079 mmol, 81%) was obtained in the same manner as in Example 1-6 from the 9-(t-butoxycarbonyloxy)-6,7-dimethoxy-3-oxo-1,3-dihydronaphtho[2,3-c]furan-4-yl trifluoromethanesulfonate prepared in Example 1-5, except for using 36.1 mg of potassium phenyltrifluoroborate (0.052 mmol) instead of potassium benzo[d][1,3]dioxol-5-yltrifluoroborate.

$^1$H NMR (400 MHz, CDCl$_3$) ⊚7.56-7.50 (m, 3H), 7.39-7.37 (m, 2H), 7.26 (s, 1H), 7.04 (s, 1H), 5.35 (s, 2H), 4.06 (s, 3H), 3.75 (s, 3H), 1.64 (s, 9H).

EXAMPLE 5-2

Synthesis of 4-hydroxy-6,7-dimethoxy-9-phenylnaphtho[2,3-c]furan-1(3H)-one [Scheme E]

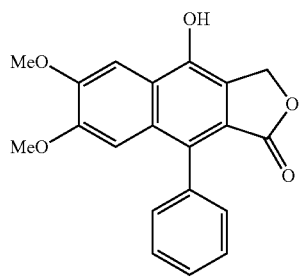 [SMILES: COc1cc2c(O)c3c(c(-c4ccccc4)c2cc1OC)C(=O)OC3]

22.2 mg of t-butyl 6,7-dimethoxy-1-oxo-9-phenyl-1,3-dihydronaphtho[2,3-c]furan-4-yl carbonate (0.051 mmol) was dissolved in 0.25 mL of dichloromethane (0.2 M) and 8.7 mg of piperidine (0.102 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na$_2$SO$_4$, filtered and then concentrated. The remainder was purified by silica gel column chromatography to obtain 11.3 mg of the target compound 4-hydroxy-6,7-dimethoxy-9-phenylnaphtho[2,3-c]furan-1(3H)-one (0.034 mmol, 66%).

$^1$H NMR (400 MHz, DMSO-d$_6$) ⊚10.43 (s, 1H), 7.51-7.43 (m, 3H), 7.32-7.30 (,2H), 6.86 (s, 1H), 5.38 (s, 2H), 3.94 (s, 3H), 3.59 (s, 3H).

EXAMPLE 5-3

Synthesis of 4,6,7-trimethoxy-9-phenylnaphtho[2,3-c]furan-1(3H)-one [Scheme F]

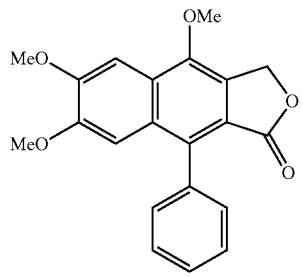 [SMILES: COc1cc2c(OC)c3c(c(-c4ccccc4)c2cc1OC)C(=O)OC3]

5.2 mg of 4-hydroxy-6,7-dimethoxy-9-phenylnaphtho[2,3-c]furan-1(3H)-one (0.015 mmol) was dissolved in 0.15 mL of N,N-dimethylformamide (0.1 M) and 3.3 mg of iodomethane (MeI) (0.023 mmol) and 4.3 mg of potassium carbonate (K2CO3) (0.031 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 5.1 mg of the target compound 4,6,7-trimethoxy-9-phenylnaphtho[2,3-c]furan-1(3H)-one (cilinaphthalide B) (0.015 mmol, 95%).

$^1$H NMR (400 MHz, CDCl$_3$) ⊚5.56 (s, 1H), 7.52-7.49 (m, 3H), 7.37-7.34 (m, 2H), 6.99 (s, 1H), 5.56 (s, 2H), 4.15 (s, 3H), 4.08(s, 3H), 3.75 (s, 3H).

EXAMPLE 6

Synthesis of 4,6,7-trimethoxy-9-(4-vinylphenyl)naphtho[2,3-c]furan-1(3H)-one

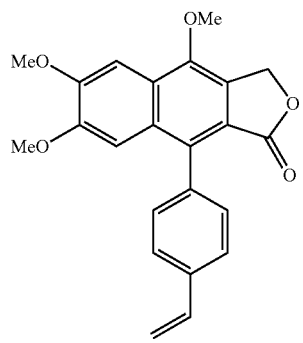 [SMILES: C=Cc1ccc(-c2c3c(c(OC)c4cc(OC)c(OC)cc24)COC3=O)cc1]

EXAMPLE 6-1

Synthesis of t-butyl 6,7-dimethoxy-1-oxo-9-(4-vinylphenyl)-1,3-dihydronaphtho[2,3-c]furan-4-yl carbonate [Scheme D]

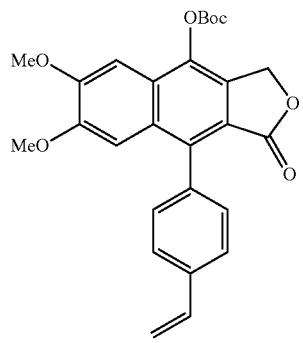

31.3 mg of the target compound t-butyl 6,7-dimethoxy-1-oxo-9-(4-vinylphenyl)-1,3-dihydronaphtho[2,3-c]furan-4-yl carbonate (0.068 mmol, 69%) was obtained in the same manner as in Example 1-6 from the 9-(t-butoxycarbonyloxy)-6,7-dimethoxy-3-oxo-1,3-dihydronaphtho[2,3-c]furan-4-yl trifluoromethanesulfonate prepared in Example 1-5, except for using 41.2 mg of potassium 4-vinylphenyltrifluoroborate (0.052 mmol) instead of potassium benzo[d][1,3]dioxol-5-yltrifluoroborate.

$^1$H NMR (400 MHz, CDCl$_3$) ⊚7.42 (d, 2H, J=8.0 Hz), 7.35 (d, 2H, J=8.0 Hz), 7.26 (s, 1H), 7.08 (s, 1H), 6.82 (dd, 1H, J=8.0, 16.0 Hz), 5.86 (dd, 1H, J=0.4, 16.0 Hz), 5.35 (s, 2H), 5.33 (dd, 1H, J=0.4, 16.0 Hz), 4.06 (s, 3H), 3.77 (s, 3H), 1.64 (s, 9H).

EXAMPLE 6-2

Synthesis of 4-hydroxy-6,7-dimethoxy-9-(4-vinylphenyl)naphtho[2,3-c]furan-1(3H)-one [Scheme E]

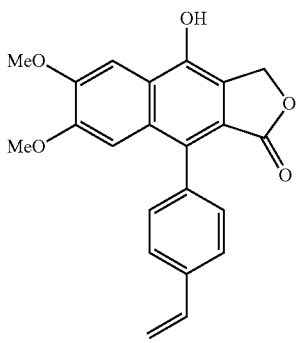 [SMILES: C=Cc1ccc(-c2c3c(c(O)c4cc(OC)c(OC)cc24)COC3=O)cc1]

20.1 mg of t-butyl 6,7-dimethoxy-1-oxo-9-(4-vinylphenyl)-1,3-dihydronaphtho[2,3-c]furan-4-yl carbonate (0.043 mmol) was dissolved in 0.22 mL of dichloromethane (0.2 M) and 7.4 mg of piperidine (0.087 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 13.9 mg of the target compound 4-hydroxy-6,7-dimethoxy-9-(4-vinylphenyl)naphtho[2,3-c]furan-1(3H)-one (0.038 mmol, 43%).

$^1$H NMR (400 MHz, DMSO-d$_6$) ⊚10.44 (s, 1H), 8.31 (s, 1H), 7.63 (s, 1H), 7.57 (d, 2H, J=8.4 Hz), 7.29 (d, 2H, J=8.0 Hz), 6.91 (s, 1H), 6.84 (dd, 1H, J=10.8, 17.6 Hz), 5.93 (d, 1H, J=18.0 Hz), 5.37 (s, 1H), 5.33 (d, 1H, J=11.2 Hz), 3.84 (s, 3H), 3.61 (s, 3H).

EXAMPLE 6-3

Synthesis of 4,6,7-trimethoxy-9-(4-vinylphenyl)naphtho[2,3-c]furan-1(3H)-one [Scheme F]

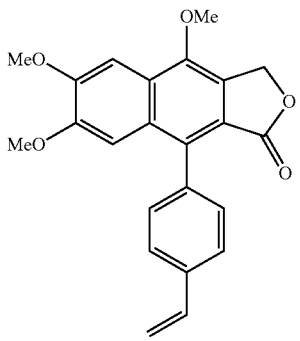 [SMILES: C=Cc1ccc(-c2c3c(c(OC)c4cc(OC)c(OC)cc24)COC3=O)cc1]

6.3 mg of 4-hydroxy-6,7-dimethoxy-9-(4-vinylphenyl)naphtho[2,3-c]furan-1(3H)-one (0.017 mmol) was dissolved in 0.17 mL of N,N-dimethylformamide (0.1 M) and 3.7 mg of iodomethane (MeI) (0.026 mmol) and 4.8 mg of potassium carbonate (K2CO3) (0.035 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 5.7 mg of the target compound 4,6,7-trimethoxy-9-(4-vinylphenyl)naphtho[2,3-c]furan-1 (3H)-one (0.015 mmol, 87%).

$^1$H NMR (400 MHz, CDCl$_3$) ⊚7.56 (d, 2H, J=8.0 Hz), 7.55 (s, 1H), 7.32 (d, 2H, J=8.0 Hz), 7.02 (s, 1H), 6.82 (dd, 1H, J=11.2, 17.6 Hz), 5.85 (d, 1H, J=17.6 Hz), 5.55 (s, 2H), 5.32 (d, 1H, J=10.8 Hz), 4.13 (s, 3H), 4.07 (s, 3H), 3.76 (s, 3H).

EXAMPLE 7

Synthesis of 9-(4-fluorophenyl)-4,6,7-trimethoxynaphtho[2,3-c]furan-1(3H)-one

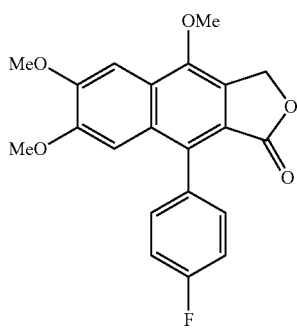 [SMILES: COc1cc2c(OC)c3c(c(-c4ccc(F)cc4)c2cc1OC)C(=O)OC3]

EXAMPLE 7-1

Synthesis of t-butyl 9-(4-fluorophenyl)-6,7-dimethoxy-1-oxo-1,3-dihydronaphtho[2,3-c]furan-4-yl carbonate [Scheme D]

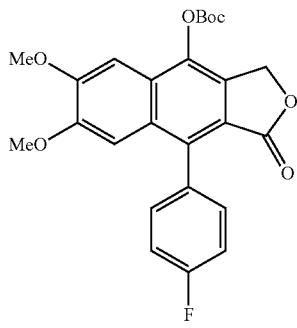

23.6 mg of the target compound t-butyl 9-(4-fluorophenyl)-6,7-dimethoxy-1-oxo-1,3-dihydronaphtho[2,3-c]furan-4-yl carbonate (0.052 mmol, 53%) was obtained in the same manner as in Example 1-6 from the 9-(t-butoxycarbonyloxy)-6,7-dimethoxy-3-oxo-1,3-dihydronaphtho[2,3-c]furan-4-yl trifluoromethanesulfonate prepared in Example 1-5, except for using 39.6 mg of potassium 4-fluorophenyltrifluoroborate (0.052 mmol) instead of potassium benzo[d][1,3]dioxol-5-yltrifluoroborate.

$^1$H NMR (400 MHz, CDCl$_3$) ⊚7.38-7.34 (m, 2H), 7.27 (s, 1H), 7.25-7.21 (m, 2H), 7.00 (s, 1H), 5.35 (s, 2H), 4.07 (s, 3H), 3.78 (s, 3H), 1.64 (s, 9H).

EXAMPLE 7-2

Synthesis of 9-(4-fluorophenyl)-4-hydroxy-6,7-dimethoxynaphtho[2,3-c]furan-1(3H)-one [Scheme E]

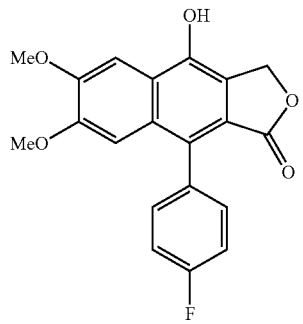 [SMILES: COc1cc2c(O)c3c(c(-c4ccc(F)cc4)c2cc1OC)C(=O)OC3]

14.0 mg of t-butyl 9-(4-fluorophenyl)-6,7-dimethoxy-1-oxo-1,3-dihydronaphtho[2,3-c]furan-4-yl carbonate (0.031 mmol) was dissolved in 0.15 mL of dichloromethane (0.2 M) and 5.2 mg of piperidine (0.062 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 8.3 mg of the target compound 9-(4-fluorophenyl)-4-hydroxy-6,7-dimethoxynaphtho[2,3-c]furan-1(3H)-one (0.023 mmol, 76%).

$^1$H NMR (400 MHz, DMSO-d$_6$) ⊚10.47 (s, 1H), 7.64 (s, 1H), 7.37-7.28 (m, 4H), 6.84 (s, 1H), 5.37 (s, 2H), 3.94 (s, 3H), 3.63 (s, 3H).

EXAMPLE 7-3

Synthesis of 9-(4-fluorophenyl)-4,6,7-trimethoxynaphtho[2,3-c]furan-1(3H)-one [Scheme F]

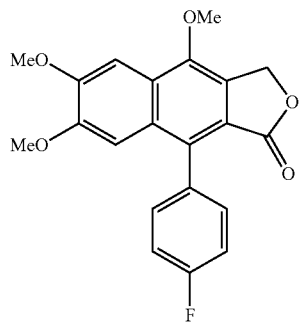 [SMILES: COc1cc2c(OC)c3c(c(-c4ccc(F)cc4)c2cc1OC)C(=O)OC3]

4.6 mg of 9-(4-fluorophenyl)-4-hydroxy-6,7-dimethoxynaphtho[2,3-c]furan-1(3H)-one (0.013 mmol) was dissolved in 0.13 mL of N,N-dimethylformamide (0.1 M) and 2.8 mg of iodomethane (MeI) (0.019 mmol) and 3.6 mg of potassium carbonate (K2CO3) (0.026 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 3.7 mg of the target compound 9-(4-fluorophenyl)-4,6,7-trimethoxynaphtho[2,3-c]furan-1(3H)-one (0.010 mmol, 78%).

$^1$H NMR (400 MHz, CDCl$_3$) ⊙7.56 (s, 1H), 7.35-7.30 (m, 2H), 7.23-7.14 (m, 2H), 6.95 (s, 1H), 5.57 (s, 2H), 4.15 (s, 3H), 4.08 (s, 3H), 3.77 (s, 3H).

EXAMPLE 8

Synthesis of 4-(9-hydroxy-6,7-dimethoxy-3-oxo-1,3-dihydronaphtho[2,3-c]furan-4-yl)benzonitrile

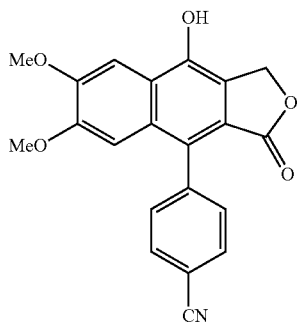 [SMILES: COc1cc2c(O)c3c(c(-c4ccc(C#N)cc4)c2cc1OC)C(=O)OC3]

EXAMPLE 8-1

Synthesis of t-butyl 9-(4-cyanophenyl)-6,7-dimethoxy-1-oxo-1,3-dihydronaphtho[2,3-c]furan-4-yl carbonate [Scheme D]

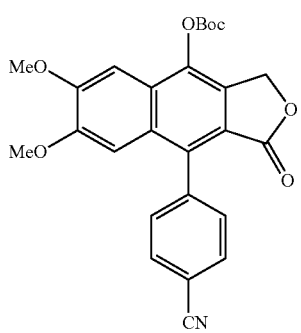

21.2 mg of the target compound t-butyl 9-(4-cyanophenyl)-6,7-dimethoxy-1-oxo-1,3-dihydronaphtho[2,3-c]furan-4-yl carbonate (0.046 mmol, 47%) was obtained in the same manner as in Example 1-6 from the 9-(t-butoxycarbonyloxy)-6,7-dimethoxy-3-oxo-1,3-dihydronaphtho[2,3-c]furan-4-yl trifluoromethanesulfonate prepared in Example 1-5, except for using 41.0 mg of potassium 4-cyanophenyltrifluoroborate (0.052 mmol) instead of potassium benzo[d][1,3]dioxol-5-yltrifluoroborate.

$^1$H NMR (400 MHz, CDCl$_3$) ⊙7.83 (d, 2H, J=8.0 Hz), 7.51 (d, 2H, J=8.4 Hz), 7.30 (s, 1H), 6.84 (s, 1H), 5.37 (s, 2H), 4.08 (s, 3H), 3.77 (s, 3H), 1.65 (s, 9H).

EXAMPLE 8-2

Synthesis of 4-(9-hydroxy-6,7-dimethoxy-3-oxo-1,3-dihydronaphtho[2,3-c]furan-4-yl)benzonitrile [Scheme E]

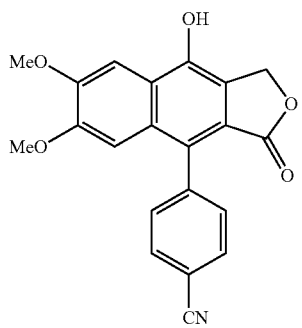 [SMILES: COc1cc2c(O)c3c(c(-c4ccc(C#N)cc4)c2cc1OC)C(=O)OC3]

11.2 mg of t-butyl 9-(4-cyanophenyl)-6,7-dimethoxy-1-oxo-1,3-dihydronaphtho[2,3-c]furan-4-yl carbonate (0.024 mmol) was dissolved in 0.12 mL of dichloromethane (0.2 M) and 4.1 mg of piperidine (0.049 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 6.5 mg of the target compound 4-(9-hydroxy-6,7-dimethoxy-3-oxo-1,3-dihydronaphtho[2,3-c]furan-4-yl)benzonitrile (0.018 mmol, 74%).

$^1$H NMR (400 MHz, DMSO-d$_6$) ⊙10.61 (s, 1H), 7.95 (d, 2H, J=8.4 Hz), 7.65 (s, 1H), 7.55 (d, 2H, J=8.0 Hz), 6.76 (s, 1H), 5.40 (s, 2H), 3.95 (s, 3H), 3.63 (s, 3H).

EXAMPLE 8-3

Synthesis of 4-(6,7,9-trimethoxy-3-oxo-1,3-dihydronaphtho[2,3-c]furan-4-yl)benzonitrile [Scheme F]

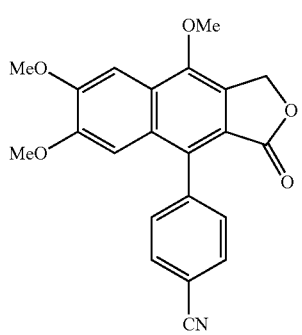

3.4 mg of 9-(4-cyanophenyl)-4-hydroxy-6,7-dimethoxynaphtho[2,3-c]furan-1(3H)-one (0.009 mmol) was dissolved in 0.09 mL of N,N-dimethylformamide (0.1 M) and 2.0 mg of iodomethane (MeI) (0.014 mmol) and 2.6 mg of potassium carbonate (K2CO3) (0.019 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 2.5 mg of the target compound 4-(6,7,9-trimethoxy-3-oxo-1,3-dihydronaphtho[2,3-c]furan-4-yl)benzonitrile (0.007 mmol, 70%).

$^1$H NMR (400 MHz, CDCl$_3$) ⊚7.82 (d, 2H, J=8.4 Hz), 7.59 (s, 1H), 7.49 (d, 2H, J=8.4 Hz), 6.80 (s, 1H), 5.60 (s, 2H), 4.17 (s, 3H), 4.08 (s, 3H), 3.76 (s, 3H).

EXAMPLE 9

Synthesis of 9-(4-acetylphenyl)-4,6,7-trimethoxynaphtho[2,3-c]furan-1(3H)-one

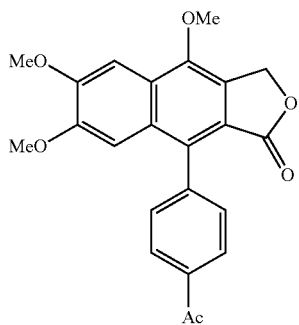

EXAMPLE 9-1

Synthesis of 9-(4-acetylphenyl)-6,7-dimethoxy-1-oxo-1,3-dihydronaphtho[2,3-c]furan-4-yl t-butylcarbonate [Scheme D]

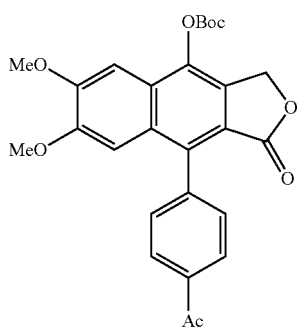

20.6 mg of the target compound 9-(4-acetylphenyl)-6,7-dimethoxy-1-oxo-1,3-dihydronaphtho[2,3-c]furan-4-yl t-butylcarbonate (0.043 mmol, 44%) was obtained in the same manner as in Example 1-6 from the 9-(t-butoxycarbonyloxy)-6,7-dimethoxy-3-oxo-1,3-dihydronaphtho[2,3-c]furan-4-yl trifluoromethanesulfonate prepared in Example 1-5, except for using 44.3 mg of potassium 4-acetylphenyltrifluoroborate (0.052 mmol) instead of potassium benzo[d][1,3]dioxol-5-yltrifluoroborate.

1H NMR (400 MHz, CDCl3) δ 8.14 (d, 2H, J=8.4 Hz), 7.51 (d, 2H, J=8.0 Hz), 7.29 (s, 1H), 6.94 (s, 1H), 5.37 (s, 2H), 4.07 (s, 3H), 3.75 (s, 3H), 2.71 (s, 3H), 1.64 (s, 9H).

EXAMPLE 9-2

Synthesis of 9-(4-acetylphenyl)-4-hydroxy-6,7-dimethoxynaphtho[2,3-c]furan-1(3H)-one [Scheme E]

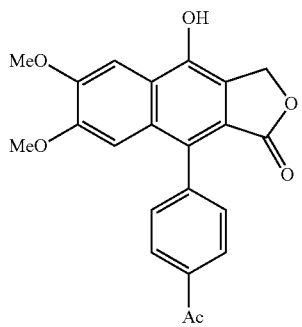 [SMILES: COc1cc2c(O)c3c(c(-c4ccc(C(C)=O)cc4)c2cc1OC)C(=O)OC3]

13.2 mg of t-butyl 9-(4-acetylphenyl)-6,7-dimethoxy-1-oxo-1,3-dihydronaphtho[2,3-c]furan-4-yl carbonate (0.028 mmol) was dissolved in 0.14 mL of dichloromethane (0.2 M) and 4.7 mg of piperidine (0.055 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 8.4 mg of the target compound 9-(4-acetylphenyl)-4-hydroxy-6,7-dimethoxynaphtho[2,3-c]furan-1(3H)-one (0.022 mmol, 80%).

$^1$H NMR (400 MHz, DMSO-d$_6$) ⊚10.55 (s, 1H), 8.07 (d, 2H, J=8.0 Hz), 7.66 (s, 1H), 7.49 (d, 2H, J=8.0 Hz), 6.83 (s, 1H), 5.40 (s, 2H), 3.95 (s, 3H), 3.61 (s, 3H).

EXAMPLE 9-3

Synthesis of 9-(4-acetylphenyl)-4,6,7-trimethoxynaphtho[2,3-c]furan-1(3H)-one [Scheme F]

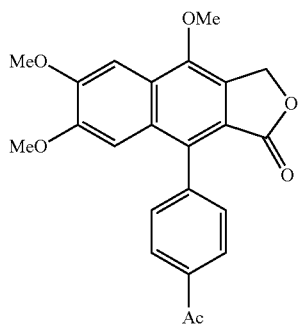 [SMILES: COc1cc2c(OC)c3c(c(-c4ccc(C(C)=O)cc4)c2cc1OC)C(=O)OC3]

4.4 mg of 9-(4-acetylphenyl)-4-hydroxy-6,7-dimethoxynaphtho[2,3-c]furan-1(3H)-one (0.012 mmol) was dissolved in 0.12 mL of N,N-dimethylformamide (0.1 M) and 2.5 mg of iodomethane (MeI) (0.017 mmol) and 3.2 mg of potassium carbonate (K2CO3) (0.023 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 3.1 mg of the target compound 9-(4-acetylphenyl)-4,6,7-trimethoxynaphtho[2,3-c]furan-1(3H)-one (0.008 mmol, 68%).

$^1$H NMR (400 MHz, CDCl$_3$) ⊙8.12 (d, 2H, J=8.4 Hz), 7.58 (s, 1H), 7.48 (d, 2H, J=8.4 Hz), 6.89 (s, 1H), 5.59 (s, 2H), 4.17 (s, 3H), 4.08 (s, 3H), 3.74 (s, 3H), 2.70 (s, 3H).

EXAMPLE 10

Synthesis of 4,6,7-trimethoxy-9-(thiophen-3-yl)naphtho[2,3-c]furan-1(3H)-one

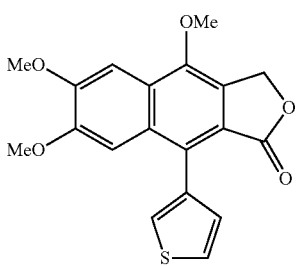

EXAMPLE 10-1

Synthesis of t-butyl 6,7-dimethoxy-1-oxo-9-(thiophen-3-yl)-1,3-dihydronaphtho[2,3-c]furan-4-yl carbonate [Scheme D]

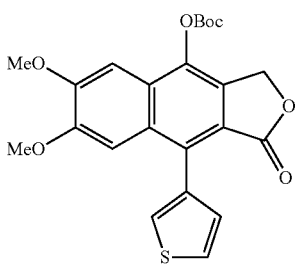

22.5 mg of the target compound t-butyl 6,7-dimethoxy-1-oxo-9-(thiophen-3-yl)-1,3-dihydronaphtho[2,3-c]furan-4-yl carbonate (0.051 mmol, 52%) was obtained in the same manner as in Example 1-6 from the 9-(t-butoxycarbonyloxy)-6,7-dimethoxy-3-oxo-1,3-dihydronaphtho[2,3-c]furan-4-yl trifluoromethanesulfonate prepared in Example 1-5, except for using 37.2 mg of potassium 4-thiophen-3-yltrifluoroborate (0.052 mmol) instead of potassium benzo[d][1,3]dioxol-5-yltrifluoroborate.

$^1$H NMR (400 MHz, CDCl$_3$) ⊙7.52 (dd, 1H, J=2.8, 4.0 Hz), 7.41 (dd, 1H, J=1.2, 2.8 Hz), 7.25 (s, 1H), 7.22 (s, 1H), 7.20 (dd, 1H, J=1.2, 4.8 Hz), 5.33 (s, 2H), 4.06 (s, 3H), 3.83 (s, 3H), 1.63 (s, 9H).

EXAMPLE 10-2

Synthesis of 4-hydroxy-6,7-dimethoxy-9-(thiophen-3-yl)naphtho[2,3-c]furan-1(3H)-one [Scheme E]

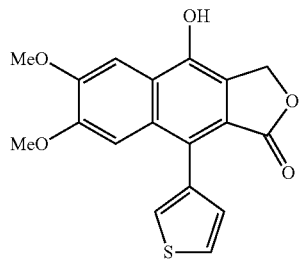

15.6 mg of t-butyl 6,7-dimethoxy-1-oxo-9-(thiophen-3-yl)-1,3-dihydronaphtho[2,3-c]furan-4-yl carbonate (0.037 mmol) was dissolved in 0.15 mL of dichloromethane (0.2 M) and 5.2 mg of piperidine (0.061 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 8.3 mg of the target compound 4-hydroxy-6,7-dimethoxy-9-(thiophen-3-yl)naphtho[2,3-c]furan-1(3H)-one (0.024 mmol, 79%).

$^1$H NMR (400 MHz, DMSO-d$_6$) ⊙10.43 (s, 1H), 7.66 (dd, 1H, J=5.2, 13.2 Hz), 7.63 (s, 1H), 7.54 (dd, 1H, J=1.2, 2.8 Hz), 7.15 (dd, 1H, J=1.2, 4.8 Hz), 5.36 (s, 2H), 3.94 (s, 3H), 3.68 (s, 3H).

EXAMPLE 10-3

Synthesis of 4,6,7-trimethoxy-9-(thiophen-3-yl)naphtho[2,3-c]furan-1(3H)-one [Scheme F]

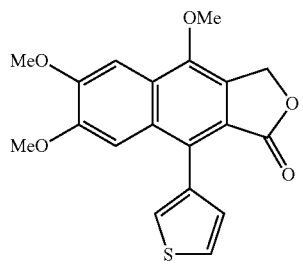

4.0 mg of 4-hydroxy-6,7-dimethoxy-9-(thiophen-3-yl)naphtho[2,3-c]furan-1(3H)-one (0.012 mmol) was dissolved in 0.12 mL of N,N-dimethylformamide (0.1 M) and 2.5 mg of iodomethane (MeI) (0.017 mmol) and 3.2 mg of potassium carbonate (K2CO3) (0.023 mmol) were sequentially added at, 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 2.9 mg of the target compound 4,6,7-trimethoxy-9-(thiophen-3-yl)naphtho[2,3-c]furan-1 (3H)-one (0.008 mmol, 70%).

$^1$H NMR (400 MHz, CDCl$_3$) ⊚7.55 (s, 1H), 7.52-7.49 (m, 1H), 7.36 (d, 1H, J=2.8 Hz), 7.17 (d, 1H, J=5.2 Hz), 7.16 (s, 1H), 5.55 (s, 2H), 4.14 (s, 3H), 4.08 (s, 3H), 3.82 (s, 3H).

EXAMPLE 11

Synthesis of 9-(furan-3-yl)-4,6,7-trimethoxynaphtho [2,3-c]furan-1(3H)-one

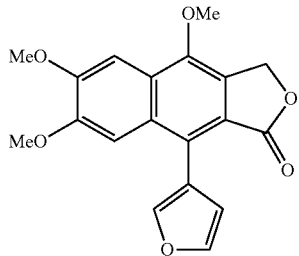 [SMILES: COc1cc2c(OC)c3c(c(-c4ccsc4)c2cc1OC)C(=O)OC3]

EXAMPLE 11-1

Synthesis of t-butyl 9-(furan-3-yl)-6,7-dimethoxy-1-oxo-1,3-dihydronaphtho[2,3-c]furan-4-yl carbonate [Scheme D]

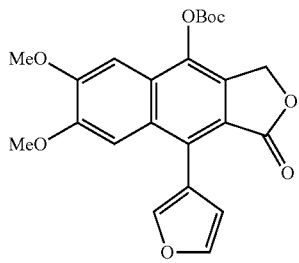

29.2 mg of the target compound t-butyl 9-(furan-3-yl)-6,7-dimethoxy-1-oxo-1,3-dihydronaphtho[2,3-c]furan-4-yl carbonate (0.069 mmol, 70%) was obtained in the same manner as in Example 1-6 from the 9-(t-butoxycarbonyloxy)-6,7-dimethoxy-3-oxo-1,3-dihydronaphtho[2,3-c]furan-4-yl trifluoromethanesulfonate prepared in Example 1-5, except for using 34.1 mg of potassium 4-furan-3-yltrifluoroborate (0.052 mmol) instead of potassium benzo[d][1,3]dioxol-5-yltrifluoroborate.

$^1$H NMR (400 MHz, CDCl$_3$) ⊚7.67-7.66 (m, 1H), 7.67 (s, 1H), 7.42 (s, 1H), 7.24 (s, 1H), 6.63-6.62 (m, 1H), 5.32 (s, 2H), 4.06 (s, 3H), 3.90 (s, 3H), 1.63 (s, 9H).

EXAMPLE 11-2

Synthesis of 9-(furan-3-yl)-4-hydroxy-6,7-dimethoxynaphtho[2,3-c]furan-1(3H)-one [Scheme E]

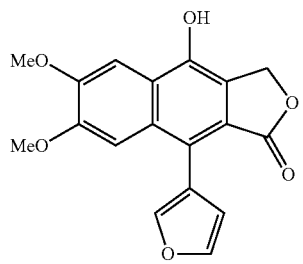 [SMILES: COc1cc2c(O)c3c(c(-c4ccoc4)c2cc1OC)C(=O)OC3]

15.6 mg of t-butyl 6,7-dimethoxy-1-oxo-9-(furan-3-yl)-1,3-dihydronaphtho[2,3-c]furan-4-yl carbonate (0.037 mmol) was dissolved in 0.18 mL of dichloromethane (0.2 M) and 6.2 mg of piperidine (0.073 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 10.5 mg of the target compound 9-(furan-3-yl)-4-hydroxy-6,7-dimethoxynaphtho[2,3-c]furan-1(3H)-one (0.032 mmol, 88%).

$^1$H NMR (400 MHz, DMSO-d$_6$) ⊚ 10.43 (s, 1H), 7.84 (s, 1H), 7.82 (s, 1H), 7.60 (s, 1H), 7.25 (s, 1H), 6.66 (s, 1H), 5.33 (s, 2H), 3.94 (s, 3H), 3.75 (s, 3H).

EXAMPLE 11-3

Synthesis of 9-(furan-3-yl)-4,6,7-trimethoxynaphtho [2,3-c]furan-1(3H)-one [Scheme F]

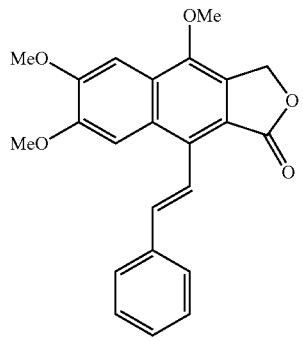 [SMILES: COc1cc2c(/C=C/c3ccccc3)c3c(c(OC)c2cc1OC)COC3=O]

5.2 mg of 9-(furan-3-yl)-4-hydroxy-6,7-dimethoxynaphtho[2,3-c]furan-1(3H)-one (0.016 mmol) was dissolved in 0.16 mL of N,N-dimethylformamide (0.1 M) and 3.4 mg of iodomethane (MeI) (0.024 mmol) and 4.4 mg of potassium carbonate (K2CO3) (0.032 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 4.2 mg of the target compound 9-(furan-3-yl)-4,6,7-trimethoxynaphtho[2,3-c]furan-1(3H)-one (0.012 mmol, 78%).

$^1$H NMR (400 MHz, CDCl$_3$) ⊚7.65 (s, 1H), 7.62 (s, 1H), 7.54 (s, 1H), 7.37 (s, 1H), 6.60 (d, 1H, J=0.8 Hz), 5.53 (s, 2H), 4.13 (s, 3H), 4.08 (s, 3H), 3.89 (s, 3H).

EXAMPLE 12

Synthesis of (E)-4,6,7-trimethoxy-9-styrylnaphtho[2,3-c]furan-1(3H)-one

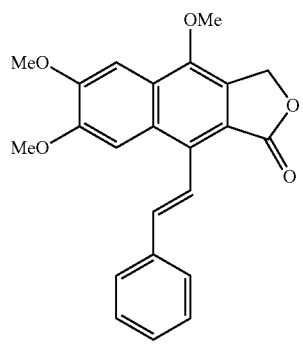 [SMILES: COc1cc2c(/C=C/c3ccccc3)c3c(c(OC)c2cc1OC)COC3=O]

EXAMPLE 12-1

Synthesis of (E)-t-butyl 6,7-dimethoxy-1-oxo-9-styryl-1,3-dihydronaphtho[2,3-c]furan-4-yl carbonate [Scheme D]

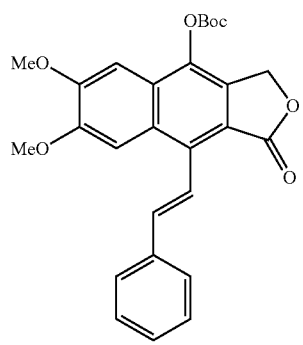

42.1 mg of the target compound (E)-t-butyl 6,7-dimethoxy-1-oxo-9-styryl-1,3-dihydronaphtho[2,3-c]furan-4-yl carbonate (0.091 mmol, 93%) was obtained in the same manner as in Example 1-6 from the 9-(t-butoxycarbonyloxy)-6,7-dimethoxy-3-oxo-1,3-dihydronaphtho[2,3-c]furan-4-yl trifluoromethanesulfonate prepared in Example 1-5, except for using 41.2 mg of potassium 4-(E)-styryltrifluoroborate (0.052 mmol) instead of potassium benzo[d][1,3]dioxol-5-yltrifluoroborate.

$^1$H NMR (400 MHz, CDCl$_3$) ⊚8.07 (d, 1H, J=16.8 Hz), 7.84 (s, 1H), 7.66-7.64 (m, 2H), 7.44-7.40 (m, 2H), 7.36-7.32 (m, 1H), 7.24 (s, 1H), 7.09 (d, 1H, J=16.8 Hz), 5.32 (s, 2H), 4.07 (s, 3H), 3.98 (s, 3H), 1.62 (s, 9H).

EXAMPLE 12-2

Synthesis of (E)-4-hydroxy-6,7-dimethoxy-9-styrylnaphtho[2,3-c]furan-1(3H)-one [Scheme E]

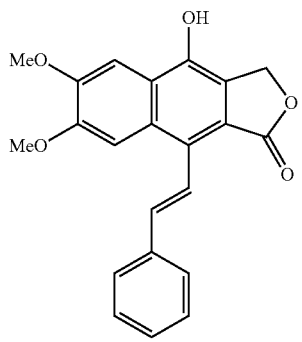 [SMILES: COc1cc2c(O)c3c(c(/C=C/c4ccccc4)c2cc1OC)C(=O)OC3]

22.7 mg of (E)-t-butyl 6,7-dimethoxy-1-oxo-9-styryl-1,3-dihydronaphtho[2,3-c]furan-4-yl carbonate (0.066 mmol) was dissolved in 0.33 mL of dichloromethane (0.2 M) and 11.2 mg of piperidine (0.132 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 22.7 mg of the target compound (E)-4-hydroxy-6,7-dimethoxy-9-styrylnaphtho[2,3-c]furan-1(3H)-one (0.063 mmol, 95%).

$^1$H NMR (400 MHz, DMSO-d$_6$) ⊚10.45 (s, 1H), 8.01 (d, 1H, J=16.4 Hz), 7.71 (s, 1H), 7.66 (d, 2H, J=7.2 Hz), 7.59 (s, 1H), 7.43 (t, 2H, J=7.2 Hz), 7.32 (t, 1H, J=7.2 Hz), 7.10 (d, 1H, J=16.8 Hz), 5.35 (s, 2H), 3.94 (s, 3H), 3.88 (s, 3H).

EXAMPLE 12-3

Synthesis of (E)-4,6,7-trimethoxy-9-styrylnaphtho[2,3-c]furan-1(3H)-one [Scheme F]

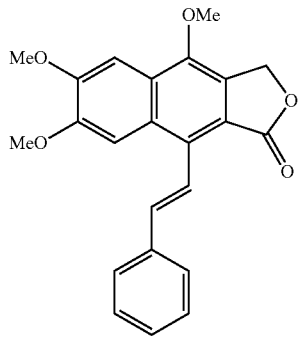 [SMILES: COc1cc2c(/C=C/c3ccccc3)c3c(c(OC)c2cc1OC)COC3=O]

10.9 mg of (E)-4-hydroxy-6,7-dimethoxy-9-styrylnaphtho[2,3-c]furan-1(3H)-one (0.030 mmol) was dissolved in 0.30 mL of N,N-dimethylformamide (0.1 M) and 6.4 mg of iodomethane (MeI) (0.045 mmol) and 8.3 mg of potassium carbonate (K2CO3) (0.060 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 10.2 mg of the target compound (E)-4,6,7-trimethoxy-9-styrylnaphtho[2,3-c]furan-1(3H)-one (0.027 mmol, 90%).

$^1$H NMR (400 MHz, CDCl$_3$) ⊚8.04 (d, 1H, J=16.8 Hz), 7.82 (s, 1H), 7.63 (d, 2H, J=7.2), 7.40 (t, 2H, J=7.2 Hz), 7.32 (t, 1H, J=7.2 Hz), 7.22 (s, 1H), 7.07 (d, 1H, J=16.8 Hz), 5.30 (s, 2H), 4.14 (s, 3H), 4.04 (s, 3H), 3.96 (s, 3H).

EXAMPLE 13

Synthesis of 5-(1,3-benzodioxol-5-yl)-9-methoxy-furo[3',4':6,7]naphtho[2,3-d]-1,3-dioxol-6(8H)-one (justicidin F, taiwanin E methyl ether)

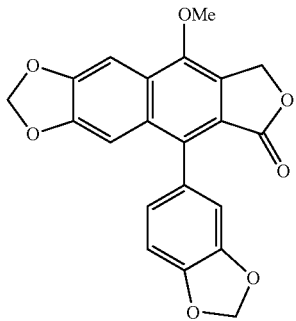 [SMILES: COc1c2c(c(-c3ccc4c(c3)OCO4)c3cc4c(cc13)OCO4)C(=O)OC2]

EXAMPLE 13-1

Synthesis of 5-bromo-6-(1,3-dioxolan-2-yl)benzo[d][1,3]dioxolane [Scheme II]

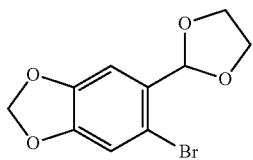 [SMILES: Brc1cc2c(cc1C1OCCO1)OCO2]

1 g of 6-bromobenzo[d][1,3]dioxol-5-carbaldehyde (4.39 mmol) was dissolved in 43.9 mL (0.1 M) of benzene and 41.8 mg of p-toluenesulfonic acid hydrate (0.22 mmol) and 817 mg of ethylene glycol (13.2 mmol) were sequentially added at 0 °C.

After connecting with a Dean-Stark trap and increasing reaction temperature to 90° C., the mixture was reacted for 5 hours. After terminating the reaction by adding 50 mL of sodium bicarbonate aqueous solution, followed by extraction with EtOAc (3×20 mL), the organic layer was washed with brine (2×5 mL), dried with anhydrous Na2SO4, filtered and then concentrated. The remainder was purified by silica gel column chromatography to obtain 1.17 g of the target compound 5-bromo-6-(1,3-dioxolan-2-yl)benzo[d][1,3]dioxolane (4.30 mmol, 98%).

$^1$H NMR (400 MHz, CDCl$_3$) ⊚7.07 (s, 1H), 7.00 (s, 1H), 6.01 (s, 1H), 5.98 (s, 2H), 4.16-4.10 (m, 2H), 4.09-4.03 (m, 2H).

EXAMPLE 13-2

Synthesis of 6-formyl-N,N-dimethylbenzo[d][1,3]dioxol-5-carboxamide [Scheme III]

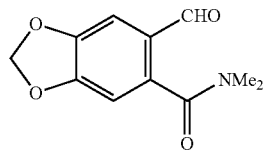 [SMILES: CN(C)C(=O)c1cc2c(cc1C=O)OCO2]

0.5 g of 5-bromo-6-(1,3-dioxolan-2-yl)benzo[d][1,3]dioxolane (1.84 mmol) was dissolved in 18.4 mL of tetrahydrofuran (0.1 M) under nitrogen atmosphere and 2.39 mL of 1.0 M n-butyllithium (2.39 mmol) was added at −78° C. After carrying out reaction at the same temperature for 30 minutes, 237 mg of N,N-dimethylcarbamoyl chloride (2.21 mmol) was added. After slowly increasing reaction temperature to 25° C., reaction was carried out for 5 hours. After lowering temperature again to 0° C., 0.92 mL of 0.5 N HCl aqueous solution was added. After carrying out reaction at the same temperature for 1 hour, the reaction was terminated by adding 10 mL of ammonium chloride aqueous solution. After extracting with EtOAc (3×5 mL), the organic layer was washed with brine (2×3 mL), dried with anhydrous Na2SO4, filtered and then concentrated. The remainder was purified by silica gel column chromatography to obtain 272 mg of the target compound 6-formyl-N,N-dimethylbenzo[d][1,3]dioxol-5-carboxamide (1.23 mmol, 67%).

$^1$H NMR (400 MHz, CDCl$_3$) ⊚9.85 (s, 1H), 7.37 (s, 1H), 6.80 (s, 1H), 6.11 (s, 2H), 3.15 (s, 3H), 2.86 (s, 3H).

EXAMPLE 13-3

Synthesis of 7-oxo-5,7-dihydroisobenzofuro[5,6-d][1,3]dioxol-5-carbonitrile [Scheme IV]

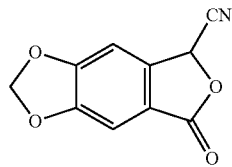 [SMILES: N#CC1OC(=O)c2cc3c(cc21)OCO3]

0.5 g of 6-formyl-N,N-dimethylbenzo[d][1,3]dioxol-5-carboxamide (2.26 mmol) was dissolved in 4.52 mL of dichloromethane (0.5 M) under nitrogen atmosphere and 44.3 mg of potassium cyanide (KCN) (0.68 mmol) and 180 mg of 18-crown-6 (0.68 mmol) were sequentially added at 0° C. After carrying out reaction at 25° C. for 30 minutes, 448 mg of trimethylsilyl cyanide (4.52 mmol) was added and reaction was carried out at 25° C. for 5 hours. After removing the organic solvent under reduced pressure, 4.52 mL of acetic acid was added and reaction was carried out at 25° C. for 12 hours. After terminating the reaction by adding 5 mL of sodium bicarbonate aqueous solution, followed by extracting with extracting with EtOAc (3×3 mL), the organic layer was washed with brine (2×2 mL), dried with anhydrous Na2SO4, filtered and then concentrated. The remainder was purified by silica gel column chromatography to obtain 427 mg of the target compound 7-oxo-5,7-dihydroisobenzofuro[5,6-d][1,3]dioxol-5-carbonitrile (2.10 mmol, 93%).

¹H NMR (400 MHz, CDCl₃) ⓢ7.23 (s, 1H), 7.04 (s, 1H), 6.22 (s, 2H), 5.98 (s, 1H).

EXAMPLE 13-4

Synthesis of t-butyl 9-hydroxy-1-oxo-1,3-dihydronaphtho[2,3-d]-1,3-dioxol[2,3-c]furan-4-yl carbonate [Scheme A+Scheme B]

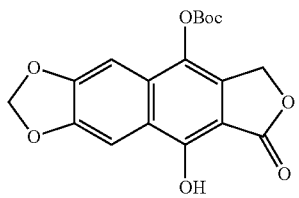

84.6 mg of 7-oxo-5,7-dihydroisobenzofuro[5,6-d][1,3]dioxol-5-carbonitrile (0.417 mmol) was dissolved in 10.4 mL of tetrahydrofuran (0.04 M) under nitrogen atmosphere and 1.25 mL of 1.0 M lithium bis(trimethylsilyl)amide (1.25 mmol) was added at −78° C. After carrying out reaction at −78° C. for 30 minutes, temperature was increased to −40° C. After adding 70.1 mg of 2(5H)-furanone (0.834 mmol), reaction was carried out at the same temperature for 30 hours. After adding 91.0 mg of t-butoxycarbonyl carbonate (Boc2O) (0.417 mmol), reaction was carried out at 25° C. for 12 hours. After terminating the reaction by adding 10 mL of ammonium chloride aqueous solution, followed by extracting with EtOAc (3×5 mL), the organic layer was washed with brine (2×3 mL), dried with anhydrous Na2SO4, filtered and then concentrated. The remainder was purified by silica gel column chromatography to obtain 85.6 mg of the target compound t-butyl 9-hydroxy-1-oxo-1,3-dihydronaphtho[2,3-d]-1,3-dioxol[2,3-c]furan-4-yl carbonate (0.238 mmol, 57%).

¹H NMR (400 MHz, CDCl₃) ⓢ8.37 (bs, 1H), 7.61 (s, 1H), 7.24 (s, 1H), 6.14 (s, 2H), 5.35 (s, 2H), 1.59 (s, 9H).

EXAMPLE 13-5

Synthesis of 9-(t-butoxycarbonyloxy)-3-oxo-1,3-dihydronaphtho[2,3-d]-1,3-dioxol[2,3-c]furan-4-yl trifluoromethanesulfonate [Scheme C]

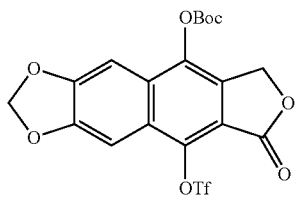

65 mg of t-butyl 9-hydroxy-1-oxo-1,3-dihydronaphtho[2,3-d]-1,3-dioxol[2,3-c]furan-4-yl carbonate (0.181 mmol) was dissolved in 3.62 mL of dichloromethane (0.05 M) under nitrogen atmosphere and 21.5 mg of pyridine (0.272 mmol) and 61.3 mg of trifluoromethanesulfonic anhydride (Tf2O) (0.217 mmol) were sequentially added at 0° C. After increasing reaction temperature to 25° C., reaction was carried out for 2 hours. After terminating the reaction by adding 3 mL of sodium bicarbonate aqueous solution, followed by extracting with EtOAc (3×2 mL), the organic layer was washed with brine (2×2 mL), dried with anhydrous Na2SO4, filtered and then concentrated. The remainder was purified by silica gel column chromatography to obtain 80.2 mg of the target compound 9-(t-butoxycarbonyloxy)-3-oxo-1,3-dihydronaphtho[2,3-d]-1,3-dioxol[2,3-c]furan-4-yl trifluoromethanesulfonate (0.163 mmol, 90%).

¹H NMR (400 MHz, CDCl₃) ⓢ7.46 (s, 1H), 7.34 (s, 1H), 6.21 (s, 1H), 5.34 (s, 1H), 1.61 (s, 9H).

EXAMPLE 13-6

Synthesis of 9-(benzo[d][1,3]dioxol-5-yl)-1-oxo-1,3-dihydronaphtho[2,3-d]-1,3-dioxol[2,3-c]furan-4-yl t-butylcarbonate [Scheme D]

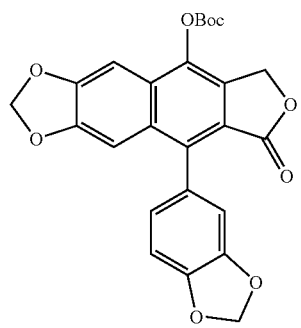

32.7 mg of the target compound 9-(benzo[d][1,3]dioxol-5-yl)-1-oxo-1,3-dihydronaphtho[2,3-d]-1,3-dioxol[2,3-c]furan-4-yl t-butylcarbonate (0.071 mmol, 98%) was obtained in the same manner as in Example 33, except for using 35.3 mg of 9-(t-butoxycarbonyloxy)-3-oxo-1,3-dihydronaphtho[2,3-d]-1,3-dioxol[2,3-c]furan-4-yl trifluoromethanesulfonate (0.072 mmol) instead of 9-(t-butoxycarbonyloxy)-6,7-dimethoxy-3-oxo-1,3-dihydronaphtho[2,3-c]furan-4-yl trifluoromethanesulfonate.

¹H NMR (400 MHz, CDCl₃) ⓢ7.32 (s, 1H), 7.11 (s, 1H), 6.83 (d, 1H, J=8.0 Hz), 6.79 (dd, 1H, J=1.2, 4.4 Hz), 6.77 (dd, 1H, J=2.0, 8.0 Hz), 6.09 (s, 2H), 6.06 (dd, 2H, J=1.2, 10.0 Hz), 5.97 (s, 2H), 1.64 (s, 9H).

EXAMPLE 13-7

Synthesis of 5-(1,3-benzodioxol-5-yl)-9-hydro-furo[3',4':6,7]naphtho[2,3-d]-1,3-dioxol-6(8H)-one (taiwanin E) [Scheme E]

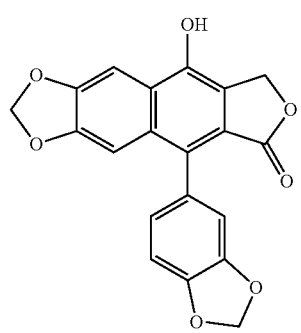 [SMILES: O=C1OCc2c1c(-c1ccc3c(c1)OCO3)c1cc3c(cc1c2O)OCO3]

20.7 mg of 9-(benzo[d][1,3]dioxol-5-yl)-1-oxo-1,3-dihydronaphtho[2,3-d]-1,3-dioxol[2,3-c]furan-4-yl t-butylcarbonate (0.042 mmol) was dissolved in 0.21 mL of dichloromethane (0.2 M) and 7.2 mg of piperidine (0.084 mmol) was added at 0° C. After increasing reaction temperature to 25° C., reaction was carried out for 5 hours. After terminating the reaction by adding 0.5 mL of 1 N hydrochloric acid aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 13.5 mg of the target compound 5-(1,3-benzodioxol-5-yl)-9-hydro-furo[3',4':6,7]naphtho[2,3-d]-1,3-dioxol-6(8H)-one (taiwanin E) (0.037 mmol, 88%).

$^1$H NMR (400 MHz, DMSO-$d_6$) ⊚10.42 (bs, 1H), 7.61 (s, 1H), 7.00 (d, 1H, J=8.0 Hz), 6.84 (s, 1H), 6.81 (d, 1H, J=1.6 Hz), 6.69 (dd, 1H, J=1.6, 8.0 Hz), 6.16 (d, 2H, J=2.0 Hz), 6.11 (d, 2H, J=11.2 Hz), 5.35 (s, 2H).

EXAMPLE 13-8

Synthesis of 5-(1,3-benzodioxol-5-yl)-9-methoxy-furo[3',4':6,7]naphtho[2,3-d]-1,3-dioxol-6(8H)-one (justicidin F, taiwanin E methyl ether) [Scheme F]

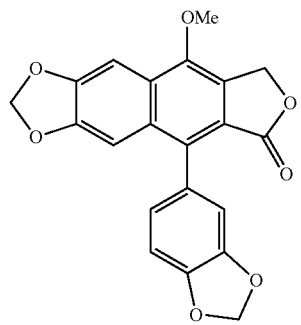 [SMILES: COc1c2c(c(-c3ccc4c(c3)OCO4)c3cc4c(cc13)OCO4)C(=O)OC2]

6.9 mg of 5-(1,3-benzodioxol-5-yl)-9-hydro-furo[3',4':6,7]naphtho[2,3-d]-1,3-dioxol-6(8H)-one (taiwanin E) (0.019 mmol) was dissolved in 0.19 mL of N,N-dimethylformamide (0.1 M) and 4.0 mg of iodomethane (MeI) (0.028 mmol) and 5.2 mg of potassium carbonate (K2CO3) (0.038 mmol) were sequentially added at 0° C. After increasing reaction temperature to 40° C., reaction was carried out for 2 hours. After terminating the reaction by adding 0.5 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 5.6 mg of the target compound 5-(1,3-benzodioxol-5-yl)-9-methoxy-furo[3',4':6,7]naphtho[2,3-d]-1,3-dioxol-6(8H)-one (justicidin F, taiwanin E methyl ether) (0.015 mmol, 78%).

$^1$H NMR (400 MHz, CDCl$_3$) ⊚7.56 (s, 1H), 7.06 (s, 1H), 6.94 (d, 1H, J=7.6 Hz), 6.77 (dd, 1H, J=1.2, 4.4 Hz), 6.75 (dd, 1H, J=1.6, 7.6 Hz), 6.08 (s, 2H), 6.06 (dd, 2H, J=1.6, 10.0 Hz), 5.51 (s, 2H), 4.09 (s, 3H).

EXAMPLE 14

Synthesis of 4-(benzo[d][1,3]dioxol-5-yl)-6,7,9-trimethoxynaphtho[2,3-c]furan-1(3H)-one (justicidin C)

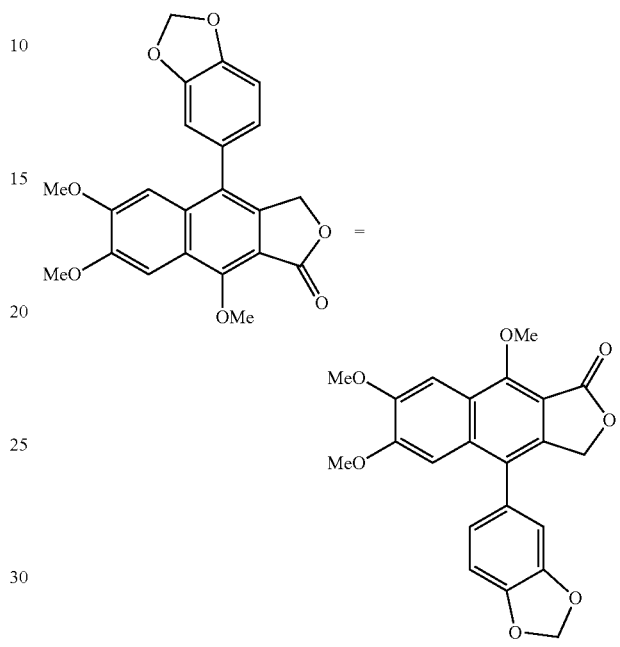

EXAMPLE 14-1

Synthesis of 9-hydroxy-6,7-dimethoxy-1-oxo-1,3-dihydronaphtho[2,3-c]furan-4-yl methanesulfonate [Scheme A+Scheme G]

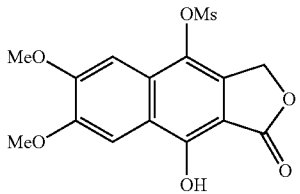 [SMILES: COc1cc2c(O)c3c(c(OS(C)(=O)=O)c2cc1OC)COC3=O]

172 mg of the 5,6-dimethoxy-3-oxo-1,3-dihydroisobenzofuran-1-carbonitrile prepared in Example 1-3 (0.79 mmol) was dissolved in 19.6 mL of tetrahydrofuran (0.04 M) under nitrogen atmosphere and 2.36 mL of 1.0 M lithium bis(trimethylsilyl)amide (2.36 mmol) was added at −78° C. After carrying out reaction at −78° C. for 30 minutes, temperature was increased to −40° C. After adding 132 mg of 2(5H)-furanone (1.57 mmol), reaction was carried out at the same temperature for 30 hours. After adding 62 mg of methanesulfonyl chloride (MsCl) (0.79 mmol), reaction was carried out at 25° C. for 12 hours. After terminating the reaction by adding 16 mL of ammonium chloride aqueous solution, followed by extracting with EtOAc (3×6 mL), the organic layer was washed with brine (2×4 mL), dried with anhydrous Na2SO4, filtered and then concentrated. The remainder was purified by silica gel column chromatography to obtain 191 mg of the target compound 9-hydroxy-6,7-dimethoxy-1-oxo-1,3-dihydronaphtho[2,3-c]furan-4-yl methanesulfonate (0.54 mmol, 69%).

$^1$H NMR (400 MHz, CDCl$_3$) ⊚7.97 (s, 1H), 6.79 (s, 1H), 5.41 (dd, 2H, J=14.4, 40.8 Hz), 3.94 (s, 3H), 3.31 (s, 3H), 3.28 (s, 3H).

EXAMPLE 14-2

Synthesis of 6,7,9-trimethoxy-1-oxo-1,3-dihydronaphtho[2,3-c]furan-4-yl methanesulfonate [Scheme H]

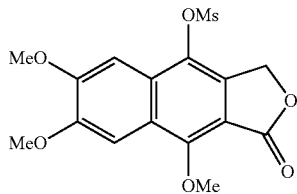 [SMILES: COc1cc2c(OS(C)(=O)=O)c3c(c(OC)c2cc1OC)C(=O)OC3]

12.7 mg of 9-hydroxy-6,7-dimethoxy-1-oxo-1,3-dihydronaphtho[2,3-c]furan-4-yl methanesulfonate (0.036 mmol) was dissolved in 0.36 mL of N,N-dimethylformamide (0.1 M) and 7.5 mg of iodomethane (MeI) (0.051 mmol) and 9.6 mg of potassium carbonate (K2CO3) (0.069 mmol) were sequentially added at 0° C. After increasing reaction temperature to 40° C., reaction was carried out for 2 hours. After terminating the reaction by adding 1.5 mL of ammonium chloride aqueous solution, followed by extracting with EtOAc (3×3 mL), the organic layer was washed with brine (2×3 mL), dried with anhydrous Na2SO4, filtered and then concentrated. The remainder was purified by silica gel column chromatography to obtain 12.6 mg of the target compound 6,7,9-trimethoxy-1-oxo-1,3-dihydronaphtho[2,3-c]furan-4-yl methanesulfonate (0.034 mmol, 96%).

$^1$H NMR (400 MHz, CDCl$_3$) ⊚7.65 (s, 1H), 7.37 (s, 1H), 5.51 (s, 2H), 4.38 (s, 3H), 4.07 (s, 3H), 4.06 (s, 3H), 3.37 (s, 3H).

EXAMPLE 14-3

Synthesis of 4-(benzo[d][1,3]dioxol-5-yl)-6,7,9-trimethoxynaphtho[2,3-c]furan-1(3H)-one (justicidin C) [Scheme I]

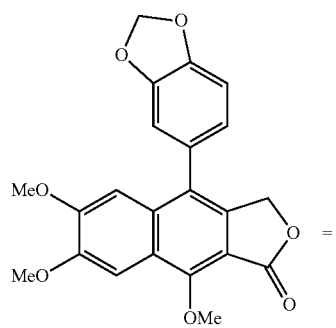

=

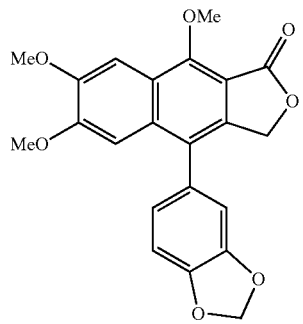

5.2 mg of 6,7,9-trimethoxy-1-oxo-1,3-dihydronaphtho[2,3-c]furan-4-yl methanesulfonate (0.014 mmol) was dissolved in 0.6 mL of 10:1 mixture solvent of dioxane and water (0.025 M) and 6.4 mg of potassium benzo[d][1,3]dioxol-5-yltrifluoroborate (0.028 mmol), 0.3 mg of palladium(II) acetate (Pd(OAc)2) (0.001 mmol), 0.8 mg of tricyclohexylphosphine (PCy3) (0.003 mmol) and 31.9 mg of cesium carbonate (Cs2CO3) (0.042 mmol) were sequentially added. After increasing reaction temperature to 80° C., reaction was carried out for 17 hours. After terminating the reaction by adding 1 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 7.2 mg of the target compound 4-(benzo[d][1,3]dioxol-5-yl)-6,7,9-trimethoxynaphtho[2,3-c]furan-1(3H)-one (justicidin C) (0.018 mmol, 77%).

$^1$H NMR (400 MHz, CDCl$_3$) ⊚7.70 (s, 1H), 6.99 (s, 1H), 6.98 (d, 1H, J=8.0 Hz), 6.87 (s, 1H), 6.81 (d, 1H, J=7.6 Hz), 6.72 (s, 2H), 5.10 (s, 2H), 4.31 (s, 3H), 3.81 (s, 3H).

EXAMPLE 15

Synthesis of 9-benzo[1,3]dioxol-5-yl-4,6,7-trimethoxy-2-methyl-2,3-dihydro-benzo[f]isoindol-1-one

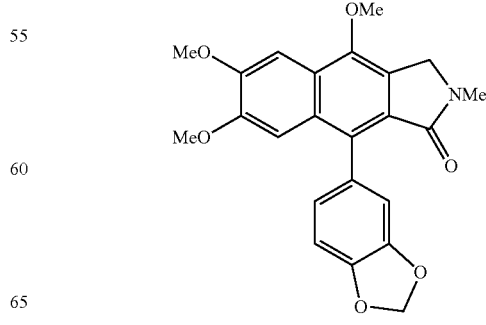

EXAMPLE 15-1

Synthesis of 1-benzo[1,3]dioxol-5-yl-3-hydroxymethyl-4,6,7-trimethoxy-naphthalene-2-carboxylic acid methylamide

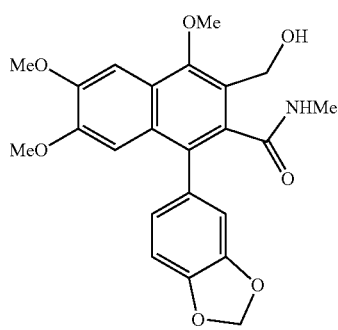 [SMILES: CNC(=O)c1c(CO)c(OC)c2cc(OC)c(OC)cc2c1-c1ccc2c(c1)OCO2]

20.1 mg of 9-(benzo[d][1,3]dioxol-5-yl)-4,6,7-trimethoxynaphtho[2,3-c]furan-1(3H)-one (0.051 mmol) was dissolved in 1.0 mL of toluene (0.05 M) and, after adding 153 μL of 1.0 M trimethylaluminum (0.153 mmol) and 10.3 mg of methylamine hydrochloride (0.153 mmol) at 0° C., reaction was carried out at 120° C. for 3 hours. After removing aluminum by passing through Celite, the remainder was purified by silica gel column chromatography to obtain 14.6 mg of the target compound of Chemical Formula 1-benzo[1,3]dioxol-5-yl-3-hydroxymethyl-4,6,7-trimethoxy-naphthalene-2-carboxylic acid methylamide (0.037 mmol, 72%).

$^1$H NMR (400 MHz, CDCl$_3$) ⊚7.50 (s, 1H), 6.99 (s, 1H), 6.96 (d, 1H, J=8.0 Hz), 6.88 (d, 1H, J=4.8 Hz), 6.85 (d, 1H, J=1.6 Hz), 6.09 (d, 2H, J=10.4 Hz), 5.31 (d, 1H, J=4.8 Hz), 4.77 (d, 2H, J=4.4 Hz), 4.11 (s, 3H), 4.07 (s, 3H), 3.82 (s, 3H), 2.69 (d, 3H, J=4.8 Hz).

EXAMPLE 15-2

Synthesis of 9-benzo[1,3]dioxol-5-yl-4,6,7-trimethoxy-2-methyl-2,3-dihydro-benzo[f]isoindol-1-one

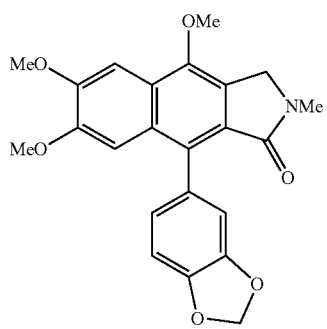 [SMILES: COc1cc2c(OC)c3c(c(-c4ccc5c(c4)OCO5)c2cc1OC)C(=O)N(C)C3]

19.7 mg of 1-benzo[1,3]dioxol-5-yl-3-hydroxymethyl-4,6,7-trimethoxy-naphthalene-2-carboxylic acid methylamide (0.050 mmol) was dissolved in 1.0 mL of 1,3-dimethyl-2-imidazolidinone (0.05 M) and, after adding 102 μL of 1.0 M isopropylmagnesium chloride (0.102 mmol) at 0° C., reaction was carried out for 30 minutes. After adding 13.1 mg of bis(dimethylamino)phosphoryl chloride (0.077 mmol) at the same temperature, reaction was carried out for 3 hours. After terminating the reaction by adding 1.0 mL of ammonium chloride aqueous solution, followed by extracting with EtOAc (3×1 mL), the organic layer was washed with brine (2×1 mL), dried with anhydrous Na2SO4, filtered and then concentrated. The remainder was purified by silica gel column chromatography to obtain 4.1 mg of the target compound 9-benzo[1,3]dioxol-5-yl-4,6,7-trimethoxy-2-methyl-2,3-dihydro-benzo[f]isoindol-1-one (0.011 mmol, 21%).

$^1$H NMR (400 MHz, CDCl$_3$) ⊚7.55 (s, 1H), 7.06 (s, 1H), 6.96 (d, 1H, J=7.6 Hz), 6.83 (d, 1H, J=1.6 Hz), 6.80 (dd, 1H, J=7.6, 1.6 Hz), 6.07 (dd, 2H, J=18.0, 1.6 Hz), 5.55 (s, 2H), 4.14 (s, 3H), 4.07 (s, 3H), 3.81 (s, 3H), 3.27 (s, 3H).

While the exemplary embodiments have been shown and described, it will be understood by those skilled in the art that various changes in form and details may be made thereto without departing from the spirit and scope of this disclosure as defined by the appended claims.

INDUSTRIAL APPLICABILITY

In synthesis of arylnaphthalene lignan compounds and derivatives according to the present disclosure, a naphthalene backbone may be constructed first and an aryl group may be introduced at the final stage. Through this, various kinds of derivatives that could not be prepared from the existing methods can be synthesized effectively. Further, the synthesis method according to the present disclosure is appropriate for large-scale production.

The invention claimed is:
1. A method for preparing a precursor of an arylnaphthalene lignan compound using Scheme A:

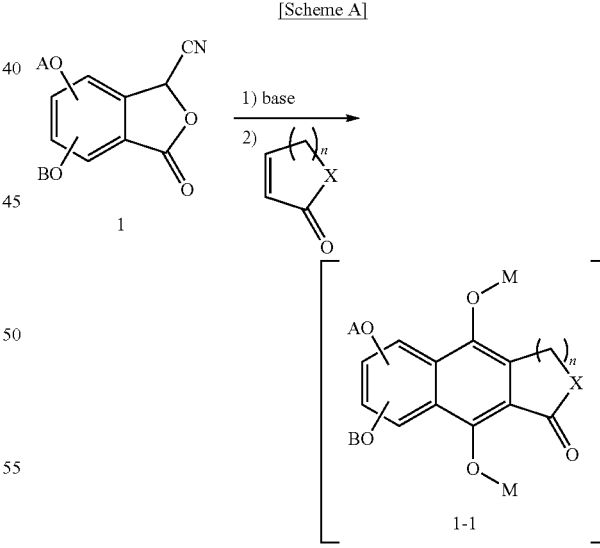

wherein
each of A and B is independently C1-C8 alkyl or C2-C9 alkylether or A and B are linked via methylene to form a heterocycle;
X is —O—, —NR1 or —CH2—;
n is 1 or 2;
R1 is C1-C8 alkyl or C7-C14 arylalkyl; and
M is lithium, potassium or sodium.

2. The method according to claim 1, wherein the aryl-naphthalene lignan compound has a structure of Chemical Formula 6 or 9:

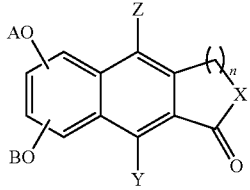

6

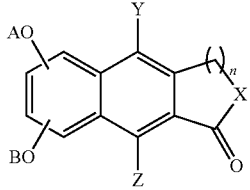

9 wherein

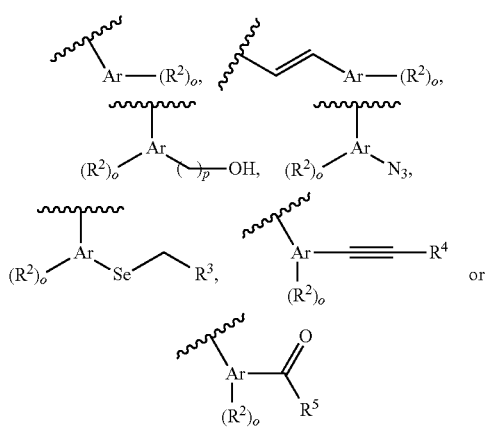

Y is hydroxyl, sulfonate,
wherein
Ar is

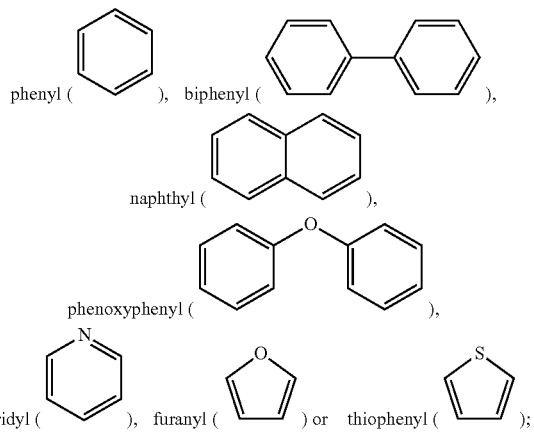

$R^2$ is hydrogen, $C_1$-$C_8$ alkyl, $C_1$-$C_4$ alkyloxy, $C_1$-$C_4$ alkylether, $C_1$-$C_4$ alkylthiooxy, vinyl, $C_3C_8$ alkylvinyl, hydroxyl, nitro (—$NO_2$), fluoro, chloro, cyano, formyl (—CHO), $C_2$-$C_{12}$ acyl, $C_1$-$C_5$ alkylester or $C_7$-$C_{10}$ arylester;

$R^3$ is $C_1$-$C_{10}$ alkyl, $C_6$-$C_{12}$aryl, $C_7$-$C_{10}$ alkylaryl, $C_2$-$C_{10}$ arylalkyl, $C_1$-$C_4$ alkylether, $C_1$-$C_5$alkylester or $C_2$-$C_{12}$ acyl;

$R^4$ is hydrogen, $C_1$-$C_6$alkyl, $C_7$-$C_{12}$cyclohexylalkyl, $C_7$-$C_{12}$arylalkyl, $C_2$-$C_6$alkylether, $C_2$-$C_6$alkylthioether, $C_2$-$C_6$ alkylcyano, $C_1$-$C_4$ alkylalcohol or

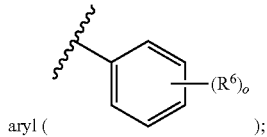

$R^5$ is independently hydrogen, $C_1$-$C_6$ alkyl, $C_7$-$C_{12}$ cyclohexylalkyl, $C_7$-$C_{12}$ arylalkyl, $C_2$-$C_6$alkylether, $C_2$-$C_6$ alkylthioether, $C_2$-$C_6$ alkylcyano, $C_1$-$C_4$alkylalcohol or

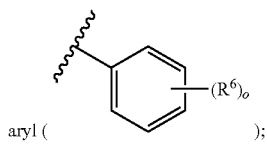

$R^6$ is hydrogen, $C_1$-$C_6$ alkyl, $C_7$-$C_{10}$) alkylaryl, $C_1$-$C_4$ alkylether, $C_1$-$C_4$ alkylthioether, fluoro or chloro;
o is an integer from 1 to 5; and
p is an integer from 0 to 2, and
Z is O—$R^7$,

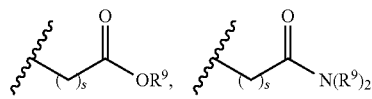

or glycosyl
wherein
$R^7$ is hydrogen, $C_1$-$C_8$ alkyl, $C_2$-$C_9$ alkylether, $C_1$-$C_5$ alkylester, $C_7$-$C_{10}$arylester or

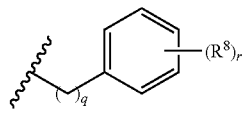

$R^8$ is $C_1$-$C_4$alkyl, $C_1$-$C_4$ alkyloxy, nitro (—$NO_2$), cyano (—CN), fluoro, chloro, bromo, iodo or hydrogen;
q is an integer from 0 to 5;
r is an integer from 1 to 4;
$R^9$ is $C_1$-$C_8$alkyl or hydrogen;
s is an integer from 1 to 5; and
the glycosyl group is 4-Oβ-D-galactopyranosyl, 4-O-α-L-arabinosyl, 4O-β-D-glucopyranosyl, 4-O-β-D-xylosyl, 6'-O-methyl-4-O-β-D-glucopyranosyl, 6'-O-methyl-4-O-β-D-galactopyranosyl, 4-O-β-D-fucopyranosyl, 6'-O-benzyl-4O-β-D-glucopyranosyl or 6'-0-benzyl-4-O-β-D-galactopyranosyl.

3. The method according to claim 1, wherein the aryl-naphthalene lignan compound is 9-(benzo[d][1,3]dioxol-5- yl)-4,6,7-trimethoxynaphtho[2,3-c]furan-1(3H)-one (justicidin A), t-butyl 9-hydroxy-6,7-dimethoxy-1-oxo-1,3-dihydronaphtho[2,3-c]furan-4-yl carbonate, 9-(t-butoxycarbonyloxy)-6,7-dimethoxy-3-oxo-1,3-dihydronaphtho[2,3-c]furan-4-yl trifluoromethanesulfonate, 9-(benzo[d][1,3]dioxol-5-yl)-6,7-dimethoxy-1-oxo-1,3-dihydronaphtho[2,3-c]furan-4-yl t-butylcarbonate, 9-(benzo[d][1,3]dioxol-5-yl)-4-hydroxy-6,7-dimethoxynaphtho[2,3-c]furan-1(3H)-one (diphyllin), 9-(3,4-dimethoxyphenyl)-4,6,7-trimethoxynaphtho[2,3-c]furan-1(3H)-one (cilinaphthalide B), t-butyl 9-(3,4-dimethoxyphenyl)-6,7-dimethoxy-1oxo-1,3-dihydronaphtho[2,3-c]furan-4-yl carbonate, 9-(3,4-dimethoxyphenyl)-4-hydroxy-6,7-dimethoxynaphtho[2,3-c]furan-1(3H)-one, 9-(3,5-dimethoxyphenyl)-4,6,7-trimethoxynaphtho[2,3-c]furan-1(3H)-one, t-butyl 9-(3,5-dimethoxyphenyl)-6,7-dimethoxy-1oxo-1,3-dihydronaphtho[2,3-c]furan-4-yl carbonate, 9-(3,5-dimethoxyphenyl)-4-hydroxy-6,7-dimethoxynaphtho[2,3-c]furan-1(3H)-one, 4,6,7-trimethoxy-9-(4-methoxyphenyl)naphtho[2,3-c]furan-1(3H)-one, t-butyl 6,7-dimethoxy-9-(4-methoxyphenyl)-1-oxo-1,3-dihydronaphtho[2,3-c]furan-4-yl carbonate, 4-hydroxy-6,7-dimethoxy-9-(4-methoxyphenyl)naphtho[2,3-c]furan-1(3H)-one, 4,6,7-trimethoxy-9-phenylnaphtho[2,3-c]furan-1(3H)-one, t-butyl 6,7-dimethoxy-1oxo-9-phenyl-1,3-dihydronaphtho[2,3-c]furan-4-yl carbonate, 4-hydroxy-6,7-dimethoxy-9-phenylnaphtho[2,3-c]furan-1(3H)-one, 4,6,7-trimethoxy-9-(4-vinylphenyl)naphtho[2,3-c]furan-1(3H)-one, t-butyl 6,7-dimethoxy-1oxo-9-(4-vinylphenyl)-1,3-dihydronaphtho[2,3-c]furan-4-yl carbonate, 4-hydroxy-6,7-dimethoxy-9-(4-vinylphenyl)naphtho[2,3-c]furan-1(3H)-one, 9-(4-fluorophenyl)-4,6,7-trimethoxynaphtho[2,3-c]furan-1(3H)-one, t-butyl 9-(4-fluorophenyl)-6,7-dimethoxy-1oxo-1,3-dihydronaphtho[2,3-c]furan-4-yl carbonate, 9-(4-fluorophenyl)-4-hydroxy-6,7-dimethoxynaphtho[2,3-c]furan-1(3H)-one, 4-(9-hydroxy-6,7-dimethoxy-3-oxo-1,3-dihydronaphtho[2,3-c]furan-4-yl)benzonitrile, t-butyl 9-(4-cyanophenyl)-6,7-dimethoxy-1oxo-1,3-dihydronaphtho[2,3-c]furan-4-yl carbonate, 4-(9-hydroxy-6,7-dimethoxy-3-oxo-1,3-dihydronaphtho[2,3-c]furan-4-yl)benzonitrile, 9-(4-acetylphenyl)-4,6,7-trimethoxynaphtho[2,3-c]furan-1(3H)-one, 9-(4-acetylphenyl)-6,7-dimethoxy-1oxo-1,3-dihydronaphtho[2,3-c]furan-4-yl t-butylcarbonate, 9-(4-acetylphenyl)-4-hydroxy-6,7-dimethoxynaphtho[2,3-c]furan-1(3H)-one, 4,6,7-trimethoxy-9-(thiophen-3-yl)naphtho[2,3-c]furan-1(3H)-one, 4-hydroxy-6,7-dimethoxy-9-(thiophen-3-yl)naphtho[2,3-c]furan-1(3H)-one, 9-(furan-3-yl)-4,6,7-trimethoxynaphtho[2,3-c]furan-1(3H)-one, t-butyl 9-(furan-3-yl)-6,7-dimethoxy-1oxo-1,3-dihydronaphtho[2,3-c]furan-4-yl carbonate, 9-(furan-3-yl)-4-hydroxy-6,7-dimethoxynaphtho[2,3-c]furan-1(3H)-one, (E)-4,6,7-trimethoxy-9-styrylnaphtho[2,3-c]furan-1(3H)-one, (E)-4-hydroxy-6,7-dimethoxy-9-styrylnaphtho[2,3-c]furan-1(3H)-one, 5-(1,3-benzodioxol-5-yl)-9-methoxy-furo[3',4':6,7]naphtho[2,3-d]-1,3-dioxol-6(8H)-one (justicidin F, taiwanin E methyl ether), t-butyl 9-hydroxy-1oxo-1,3-dihydronaphtho[2,3-d]-1,3-dioxol[2,3-c]furan-4-yl carbonate, 9-(t-butoxycarbonyloxy)-3-oxo-1,3-dihydronaphtho[2,3-d]-1,3-dioxol[2,3-c]furan-4-yl trifluoromethanesulfonate, 9-(benzo[d][1,3]dioxol-5-yl)-1-oxo-1,3-dihydronaphtho[2,3-d]-1,3-dioxol[2,3-c]furan-4-yl t-butylcarbonate, 5-(1,3-benzodioxol-5-yl)-9-hydro-furo[3',4':6,7]naphtho[2,3-d]-1,3-dioxol-6(8H)-one (taiwanin E), 4-(benzo[d][1,3]dioxol-5-yl)-6,'7,9-trimethoxynaphtho[2,3-c]furan-1(3H)-one (justicidin C), 9-hydroxy-6,7-dimethoxy-1oxo-1,3-dihydronaphtho[2,3-c]furan-4-yl methanesulfonate, 6,7,9-trimethoxy-1oxo-1,3-dihydronaphtho[2,3-c]furan-4-yl methanesulfonate or 9-benzo[1,3]dioxol-5-yl-4,6,7-trimethoxy-2-methyl-2,3-dihydro-benzo[f]isoindol-1-one.

4. The method according to claim 1, wherein Scheme A comprises:

Michael reaction;

aldol reaction; and benzannulation.

5. The method according to claim 1, wherein the base in Scheme A is one or more selected from a group consisting of lithium bis(trimethylsilyl)amide, potassium bis(trimethylsilyl)amide, sodium bis(trimethylsilyl)amide, lithium t-butoxide, potassium t-butoxide, sodium t-butoxide, lithium diisopropylamide, s-butyllithium and t-butyllithium.

6. The method according to claim 1, wherein, in Scheme A, the α,β-unsaturated carbonyl compound

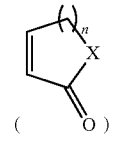

is used in an amount of 1.0-3.0 equivalents based on the compound of Chemical Formula 1.

7. A method of preparing an arylnaphthalene lignan compound, the method comprising:

forming a precursor of an arylnaphthalene lignan compound by the method according to claim 2, and forming the arylnaphthalene lignan compound using the precursor of the arylnaphthalene lignan compound, wherein the arylnaphthalene lignan compound is the compound of Chemical Formula 6, and the forming the arylnaphthalene lignan compound comprises Schemes B, C and D sequentially following Scheme A:

[Scheme B]

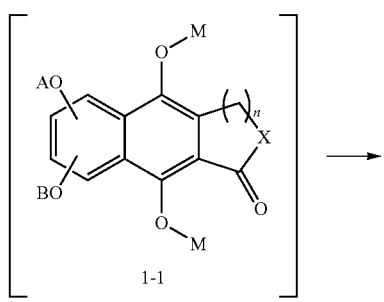

1-1

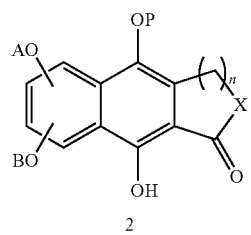

2

[Scheme C]

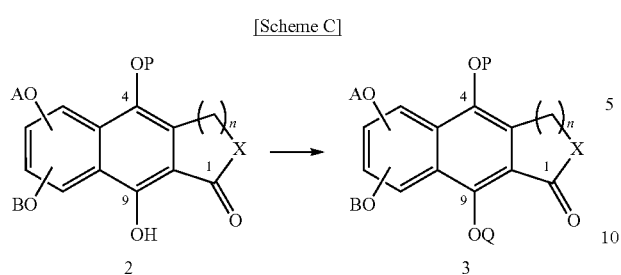

[Scheme D]

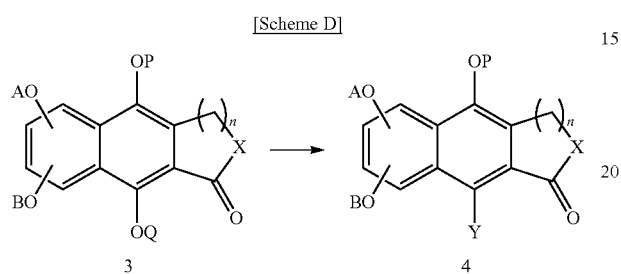

wherein
P is a protecting group of a hydroxyl group;
Q is sulfonyl; and
Scheme D is a Suzuki-Miyaura reaction.

8. The method according to claim 7, wherein the preparation method further comprises Scheme E of deprotecting the protecting group of the hydroxyl group at 4-position of the compound of Chemical Formula 4 following Scheme D:

[Scheme E]

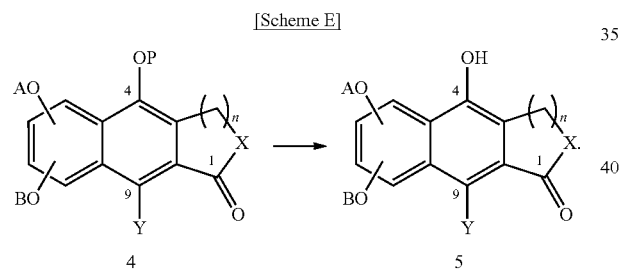

9. The method according to claim 8, wherein the preparation method further comprises Scheme F of converting the hydroxyl group of the compound of Chemical Formula 5 to Z following Scheme E:

[Scheme F]

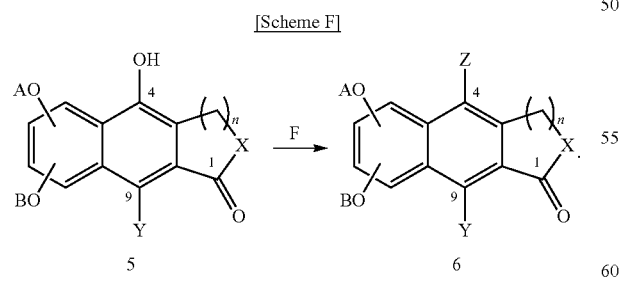

10. A method for preparing an arylnaphthalene lignan compound, the method comprising:
forming a precursor of an arylnaphthalene lignan compound by the method according to claim 2, and
forming the arylnaphthalene lignan compound using the precursor of the arylnaphthalene lignan compound, wherein the arylnaphthalene lignan compound is the compound of Chemical Formula 9, and the forming of the arylnaphthalene lignan compound comprises Schemes G, H and I sequentially following Scheme A:

[Scheme G]

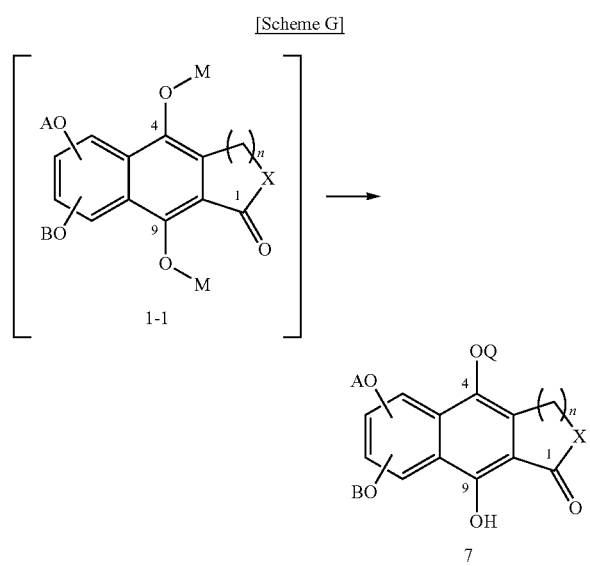

[Scheme H]

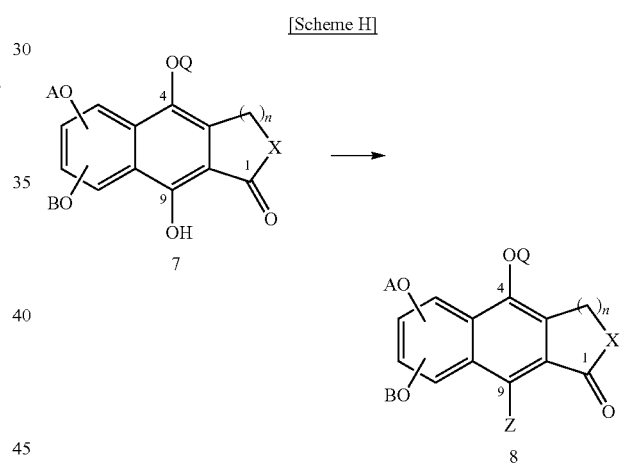

[Scheme I]

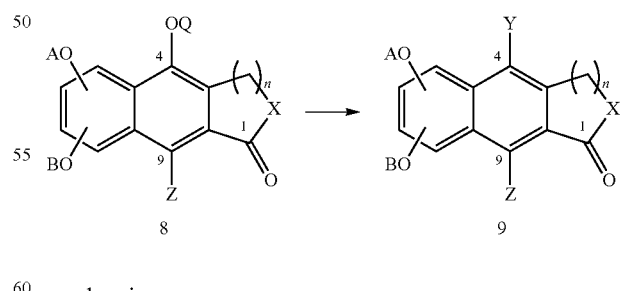

wherein
Q is sulfonyl; and
Scheme I is a Suzuki-Miyaura reaction.

11. The method according to claim 7,
wherein the sulfonyl group Q is $SO_2R^{10}$; and
wherein $R^{10}$ is methyl, trifluoromethyl, methylphenyl or nitrophenyl.

12. The method according to claim 8,
 wherein the sulfonyl group Q is $SO_2R^{10}$; and
wherein $R^{10}$ is methyl, trifluoromethyl, methylphenyl or nitrophenyl.

13. The method according to claim 9,
 wherein the sulfonyl group Q is $SO_2R^{10}$; and
wherein $R^{10}$ is methyl, trifluoromethyl, methylphenyl or nitrophenyl.

14. The method according to claim 10,
 wherein the sulfonyl group Q is $SO_2R^{10}$; and
wherein $R^{10}$ is methyl, trifluoromethyl, methylphenyl or nitrophenyl.

* * * * *